(12) United States Patent
Makrigiorgos

(10) Patent No.: US 7,247,428 B2
(45) Date of Patent: Jul. 24, 2007

(54) METHODS FOR RAPID SCREENING OF POLYMORPHISMS, MUTATIONS AND METHYLATION

(75) Inventor: Gerrasimos M. Makrigiorgos, Brookline, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 581 days.

(21) Appl. No.: 10/179,053

(22) Filed: Jun. 25, 2002

(65) Prior Publication Data

US 2003/0022215 A1  Jan. 30, 2003

Related U.S. Application Data

(63) Continuation of application No. PCT/US02/12709, filed on Apr. 22, 2002.

(60) Provisional application No. 60/285,796, filed on Apr. 23, 2001.

(51) Int. Cl.
*C12Q 1/68*  (2006.01)
*C12P 19/34*  (2006.01)

(52) U.S. Cl. .................. 435/6; 435/91.1; 435/91.2

(58) Field of Classification Search .................. 435/6
See application file for complete search history.

(56) References Cited

U.S. PATENT DOCUMENTS

| | | | | |
|---|---|---|---|---|
| 5,183,752 | A * | 2/1993 | Markwell et al. ........... 435/196 |
| 5,459,039 | A | 10/1995 | Modrich et al. | |
| 5,571,676 | A * | 11/1996 | Shuber ............................. 435/6 |
| 5,707,806 | A | 1/1998 | Shuber | |
| 5,824,471 | A * | 10/1998 | Mashal et al. ................. 435/6 |
| 5,919,623 | A | 7/1999 | Taylor | |
| 5,976,798 | A * | 11/1999 | Parker et al. ................... 435/6 |
| 6,045,994 | A * | 4/2000 | Zabeau et al. ................. 435/6 |
| 6,174,680 | B1 | 1/2001 | Makrigiorgos | |
| 6,218,152 | B1 | 4/2001 | Auerbach | |

FOREIGN PATENT DOCUMENTS

| | | | |
|---|---|---|---|
| WO | WO 99/27085 | * | 6/1999 |
| WO | WO 00/39345 | | 7/2000 |

OTHER PUBLICATIONS

Chakrabarti et al. Cancer Research. vol. 60, pp. 732-737, Jul. 15, 2000.*
T.A. Brown, Molecular Biology LabFax, Bios Scientific Publishers, Blackwell Scientific Publication, San Diego, California, p. 155, Dec. 1991.*
Myers et al., *Methods in Enzymology*, 155:501-527 (1987).
Borresen et al., *Proc. Nat. Acad. Sci. USA*, 88:8405-8409 (1991).
Orita et al., *Proc. Nat. Acad. Sci. USA*, 86:2766-2770 (1989).
Nagamine et al., *Am. J. Hum., Genet.*, 45:337-339 (1989).
Roest et al., *Hum. Molec. Genet.*, 2:1719-1721 (1993).
Zafiropoulos et al., *Biotechniques*, 23:1104-1109 (1997).
Lewis et al., *Biotechniques*, 24:102-110 (1998).
Cotton et al., *Proc. Natl. Acad. Sci., USA*, 85:4397-4401 (1988).
Nelson et al., *Nature Genetics*, 4:11-18 (1993).
Nollau et al., *Clinical Chemistry*, 43:1114-1128 (1997).
Wodicka, *Nature Biotechnology*, 15:1359-1367 (1997).
Lockhart, D.J., *Nature Biotechnology*, 14:1675-1680 (1996).
Schena, M., *Trends Biotennol.*, 16:301-306 (1998).
Yang, T.T., *Biotechniques*, 18:498-503 (1995).
Ginot, F., *Human Mutation*, 10:1-10 (1997).
Wang, D.G., *Science*, 280:1077-1082 (1998).
Sidransky, D., *Science*, 278:1054-1058 (1997).
Lipshutz, R.J., *Biotechniques*, 19:442-448 (1995).

* cited by examiner

*Primary Examiner*—Young J. Kim
(74) *Attorney, Agent, or Firm*—Nixon Peabody LLP

(57) ABSTRACT

The present method is directed to methods of detecting mismatches, polymorphisms, and methylation in multiple genes or the same gene in multiple individuals.

17 Claims, 10 Drawing Sheets

DETECTION OF TRACES OF G→A MUTATIONS IN Ku GENE
USING PCR-RFLP-PCR (PRIMER LIGATION) APPROACH

LANE 1: 1 : 4 MUTANT:NORMAL SAMPLE.
LANE 2: NORMAL SAMPLE.
LANE 3: 1:200
LANE 4: 1:2,000 MUTANT:NORMAL SAMPLE
LANE 5: 1:20,000 MUTANT:NORMAL SAMPLE

SEQUENCE LISTING

```
<160> NUMBER OF SEQ ID NOS: 5

<210> SEQ ID NO 1
<211> LENGTH: 4
<212> TYPE: DNA
<213> ORGANISM: artificial sequence
<220> FEATURE:
<223> OTHER INFORMATION: restriction enzyme site

<400> SEQUENCE: 1 gatc                                                                    4

<210> SEQ ID NO 2
<211> LENGTH: 6
<212> TYPE: DNA
<213> ORGANISM: artificial sequence
<220> FEATURE:
<223> OTHER INFORMATION: restriction enzyme site

<400> SEQUENCE: 2 gatatc                                                                  6

<210> SEQ ID NO 3
<211> LENGTH: 6
<212> TYPE: DNA
<213> ORGANISM: artificial sequence
<220> FEATURE:
<223> OTHER INFORMATION: example of common sequence

<400> SEQUENCE: 3 gggggg                                                                  6

<210> SEQ ID NO 4
<211> LENGTH: 15
<212> TYPE: DNA
<213> ORGANISM: artificial sequence
<220> FEATURE:
<223> OTHER INFORMATION: oligonucleotide primer

<400> SEQUENCE: 4
tgtaaaacga cggcc                                                       15

<210> SEQ ID NO 5
<211> LENGTH: 19
<212> TYPE: DNA
<213> ORGANISM: artificial sequence
<220> FEATURE:
<223> OTHER INFORMATION: oligonucleotide primer

<400> SEQUENCE: 5
aggaaacagc tatgaccat                                                   19
```

METHODS FOR RAPID SCREENING OF POLYMORPHISMS, MUTATIONS AND METHYLATION

CROSS-REFERENCE TO RELATED APPLICATION

This application is a continuation of co-pending International Application PCT/US02/12709, filed on 22 Apr. 2002 which designated the U.S and which claims the benefit of U.S. Provisional Application No. 60/285,796, filed 23 Apr. 2001, the content of which is relied upon and incorporated herein by reference in its entirety.

FIELD OF THE INVENTION

The present invention is directed to methods for rapid screening of polymorphisms, mutations, and methylation in a nucleic acid when compared to a control sequence. The method can be used to detect multiple deletions, insertions, substitutions, single base changes and sequence changes associated with methylation. In a preferred embodiment the method can be used to rapidly identify multiple mutations and/or polymorphisms in a nucleic acid segment, or in an arbitrary mixture of nucleic acid segments or genes.

BACKGROUND OF THE INVENTION

The detection of changes in nucleic acid sequences such as exhibited by mutations and methylation has been an area of great interest in recent years. For example, mutations in certain genes have been associated with a variety of disorders—ranging from blood disorders to cancers. Genetic tests are thus becoming an increasingly important facet of medical care. Consequently, there has been an emphasis on the ability to rapidly and efficiently detect mutations and polymorphisms.

Many electrophoretic techniques have been developed to rapidly screen DNAs for sequence differences by which such mutations can be detected. Denaturing Gradient Get Electrophoresis (DGGE) [Myers, R. M., Maniatis, T. and Lerman, L., *Methods in Enzymology*, 155, 501-527 (1987)], Constant Denaturant Gel Electrophoresis (CDGE) [Borresen, A. L., et al., Proc. Nat. Acad. Sci. USA, 88, 8405 (1991)], Single Strand Conformation Polymorphism (SSCP) [Orrita, M., et al., *Proc. Nat. Acad. Sci. USA*, 86, 2766-2770 (1989)], Heteroduplex Analysis (HA) [Nagamine, C. M., et al., *Am. J. Hum, Genet.*, 45,377-399 (19?9)] and Protein Truncation Test (PTT) [Roest, P. A. M., et al., Hum. Molec. Genet., 2,1719-1721 (1993)] are frequently used methods. Many labs use combinations of these methods to maximize mutation detection efficiency. All these methods require gel electrophoresis. Methods that do not require gel electrophoresis also exist. For example, selective hybridization on immobilized target sequences allows screening for rare known mutations [Zafiropoulos, A., et al., *Biotechniques* 223, 1104-1109 (1997)], while mass-spectrometry has been used to detect mutations by analyzing molecular weight of proteins [Lewis, J. K., et al., *Biotechniques* 24, 102-110 (1998)].

A fundamental problem with most currently existing mutation and polymorphism detection methods is that they only screen for mutations in a single gene at a time (i.e. the method is directed to looking at a 'gene of interest', that is suspected of having a mutation). Given that the human genome has 35,000-100,000 genes, this is a severe limitation. It is likely that unknown mutations and polymorphisms in several other genes both known and unknown, exist simultaneously with mutations/polymorphisms in the 'gene of interest'. However, mutations in those other genes would likely not be identified. Therefore a method that can perform 'mutation/polymorphism scanning' in a wide array of genes simultaneously, without the initial need for identifying the gene one is screening, would be useful. Gel-electrophoresis—based methods are essentially restricted to examining mutations in a single gene at a time. Attempts have been made to devise non-gel electrophoretic methods to identify mutations, that would not be restricted to a single gene [Cotton et al., *Proc. Natl. Acad. Sci. USA* vol. 85, pp 4397-4401, (1988)] [Nelson, S. F. et al., *Nature Genetics*, 4, 11-8, (May 1993)] [Modrich, P., et al., Methods for Mapping Genetic Mutations. U.S. Pat. No. 5,459,039, (1995)]. These methods, however, have had limited success (Nollau P. and Wagener C., *Clinical Chemistry* 43:1114-1128 (1997)) since they are complicated, typically requiring several enzymatic steps, and they result in a large number of false positives, i.e. they frequently score mutations and polymorphisms in normal DNA. It would be desirable to have a method that allows highly sensitive and specific identification and rapid purification of sites that contain mutation/polymorphism over large spans of the genome.

Although DNA arrays and methodologies that can simultaneously scan a large set of DNA fragments for gene expression (e.g. the 'repertoire' and amount of genes expressed in normal vs. cancer cells) are known [Wodicka L, *Nature Biotechnology* 15: 1359-1367 (1997); Lockhart, D J, *Nature Biotechnology* 14: 1675-1680 (1996); Schena, M., *Trends Biotecnnol* 16: 301-306, (1998); Yang, T. T., *Biotechniques* 18: 498-503, (1995)], the ability to scan a large set of random DNA fragments for unknown mutations is a much more demanding process for which the technology is lagging [Ginot F., *Human Mutation* 10: 1-10 (1997)]. Thus far DNA array-based methods to scan for polymorphisms (SNPs) and mutations has been restricted to specific genes [Lipshutz, R. J., *Biotechniques* 19: 442-447 (1995); Wang, D. G., *Science* 280: 1077-1082 (1998)]. Whereas detection of unknown mutations over several genes requires a selectivity and sensitivity not currently achievable by present arrays [Ginot F., *Human Mutation* 10: 1-10 (1997)]. For example, when it comes to unknown mutation detection, even a single gene with a coding sequence of the size of APC (8.5 of kb) is difficult to screen in a single experiment, especially when an excess normal alleles is simultaneously present [Sidransky D., *Science* 278: 1054-1058 (1997)]. Thus, current arrays do not scan whole genes from the 5' to the 3' end, but selectively sample the gene. For example, expression arrays are biased to the 3' end. U.S. Pat. No. 6,174,680 described a method and an array that could be used to screen and identify a plurality of changes. However, additional methods for identifying changes are desirable. It would also be desirable to have a number of methods that could sample genes over larger portions of a gene and multiple genes. A method that permits identification of additions, substitutions, deletions, methylation and glycosylation changes over large spans of the genome would also be desirable.

SUMMARY OF THE INVENTION

We have found a method that permits one to overcome resolutions and other limitations existing in current DNA chip technology and utilize a range of existing technology to rapidly scan hundreds or thousands of genes simultaneously to identify changes in these sequences when compared to a control sequence. For example, the control can be a wild type sequence. The changes can include additions, substitutions, insertions and deletions. In this manner, a wide range of changes as compared to the wild type can be determined. For example, polymorphisms and mutations. One can also identify other changes such as methylations. The method can be used to identify (50-1000 bases) DNA segments that contain mutations or polymorphisms in a single gene or in multiple genes simultaneously. This method comprises:

preparing the target nucleic acid and a control nucleic acid;

hybridizing the target nucleic acid with a control nucleic acid to create a heteroduplex, wherein the control nucleic acid is the wild type nucleic acid corresponding to the target nucleic acid;

removing any 5' phosphate groups or 3' hydroxyl groups from the DNA ends;

cleaving the nucleic acid at the site of any mismatch or methylation in said heteroduplex using any agent that generates a single or a double strand break at the sites of mismatch or methylation;

ligating a linker at the 5' phosphate group at the newly generated 5' phosphate group(s) at the site of cleavage if 5' phosphate groups have been removed, or ligating a linker at the newly generated 3' hydroxyl group(s) at the site of cleavage if 3' hydroxyl groups have been removed; and selectively amplifying the nucleic acid fragments which have a linker ligated thereto using polymerase chain reaction.

Accordingly, instead of selecting a single gene at a time and examining whether it contains a change, the present methodology first scans the entire DNA to identify and isolate all DNA fragments which contain mismatches. Once such fragments have been identified, one can do a number of things such as determine which genes these DNA fragments belong to, for example by using available DNA arrays. Thus, the search for mutations is transformed to the easier task of searching for genes on a DNA array to identify where a mismatch occurs. Accordingly, DNA arrays currently used for multiplexed gene expression scanning [Wodicka L, *Nature Biotechnology* 15: 1359-1367 (1997); Lockhart, D J, *Nature Biotechnology* 14: 1675-1680 (1996).; Schena, M., *Trends Biotecnnol* 16: 301-306, (1998); Yang, T. T., *Biotechniques* 18: 498-503, (1995)] can be used directly or with minor modifications known to the artisan based upon this disclosure to scan for alterations in a target nucleic acid(s).

DETAILED DESCRIPTION OF THE INVENTION

Figure 1:
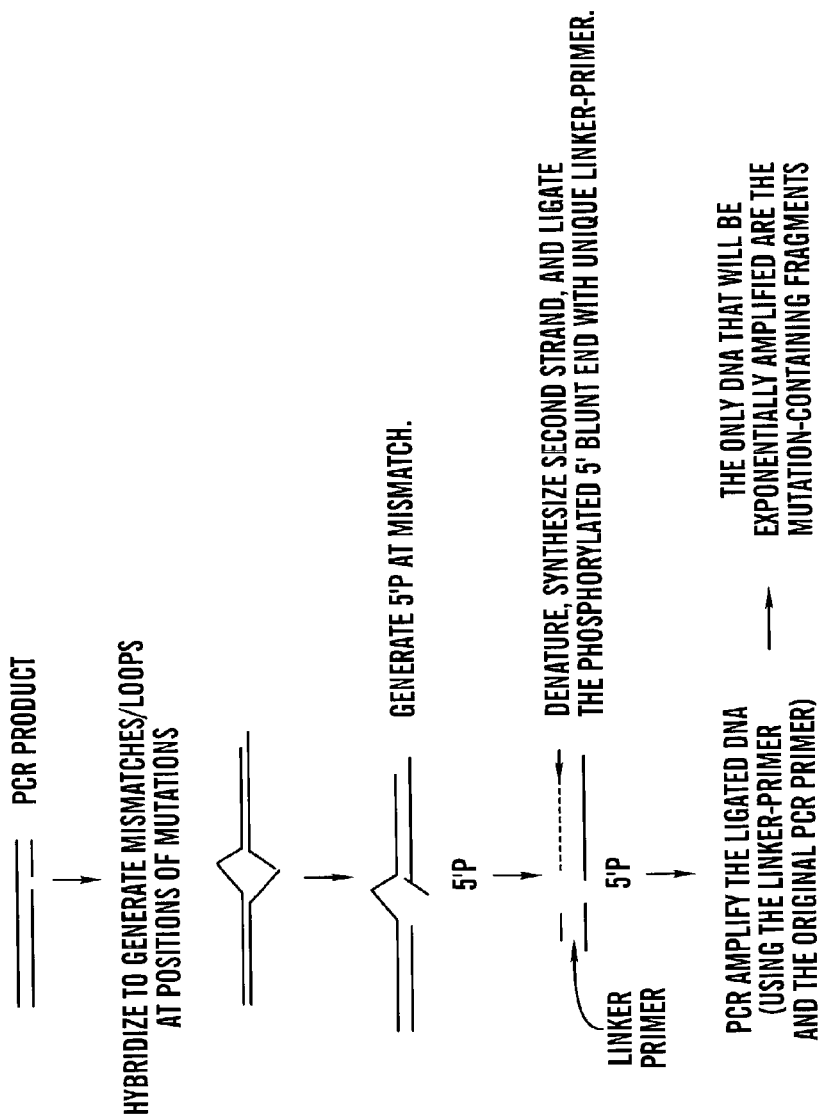
FIG. 1 shows a schematic of how the present technology is applied to identify mutations in a single known gene.
Figure 2:
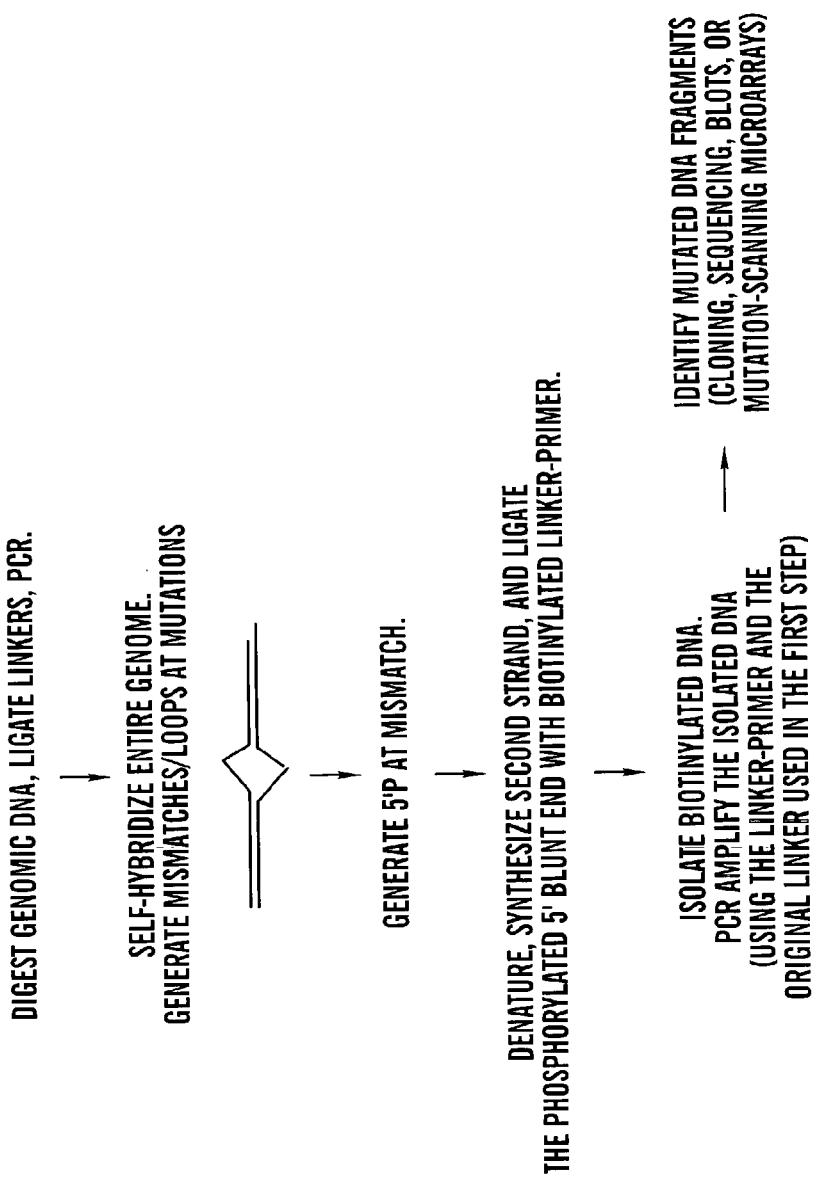
FIG. 2 shows a schematic of how the present technology is applied to screen for mutations in many genes simultaneously, such as using genomic DNA.

The present invention provides biochemical methods for identifying multiple changes in a nucleic acid, for example, a target DNA sequence as compared to a control sequence, e.g., the wild type sequence. These changes include additions, deletions, and substitutions. The changes can result in polymorphisms or mutations. One can also identify further such changes as methylation sites, glycosylation sites, etc. Consequently, one can deduce a range of changes that result from the changes identified. The methods for detecting alterations such as polymorphisms, mutations, and methylation sites can be applied to a single known target gene or for screening for alterations in a complex target mixture of many genes, for example the entire genome. Preferably, one is looking at changes in a plurality of genes. Preferably, at least five genes.

For example, in trying to detect unknown mutations it has thus far proven difficult to screen for a single gene of about 8.5 kb (such as APC) in a single experiment, especially when an excess of normal alleles is simultaneously present [Sidransky, D. *Science* 278: 1054-1058 (1997)]. By contrast, the present method can be used to screen multiple genes at once and/or multiple individuals, and selects and isolates only those fragments containing a mutation or polymorphism. Similarly, the method can be used to screen for site changes such as methylation, in a single gene or a complex mix of many genes.

To detect these alterations in a nucleic acid(s), the method of the present invention involves: 1) preparing nucleic acid template(s); 2) hybridizing the nucleic acid template(s) to control template(s) to form heteroduplexes; 3) removing any existing 5' phosphate groups (or in an alternative embodiment, 3' hydroxyl groups); 4) cleaving the template(s) at sites of mismatch using chemical or enzymatic agents to generate a strand break at the site of mismatch; 5) separating the heteroduplex and synthesizing second strands; 6) ligating linkers at the sites of cleavage; and 7) performing PCR amplification of the target nucleic acids containing alterations. Preferably, the strand break at the site of mismatch contains a 5' phosphate at the end, sometimes referred to as a 5' P end. (In the alternative embodiment, wherein 3' OH groups, sometimes referred to as 3' hydroxyl groups, are removed, the strand break is designed to have a 3' OH).

The method of the present invention isolates the mismatch-containing nucleic acids from the remaining unchanged nucleic acid segments and amplifies them. As a result of this selection for mismatch-containing segments, it does not matter the extent to which, for example, normal alleles outnumber aberrant segments. This permits screening multiple genes at a single time. Preferably, at least five genes. More preferably, at least 8 genes. Still more preferably, at least 10 genes.

The method of the present invention typically comprises the following steps. As explained, infra, some variation on these steps can be practiced.

Step 1: Preparing Nucleic Acid Templates

The target nucleic acid can be from any source, such as a PCR product of a known gene or a preparation of genomic DNA. The preferred target nucleic acid is DNA, but mRNA can also be used. The DNA can be any mixture containing one or various sizes of DNA, such as cDNA synthesized from the whole mRNA collected from cells that need to be screened for mutation/polymorphism; or fractions thereof; or the whole genomic DNA collected from cells that need to be screened for mutation/polymorphism; or fractions thereof; or any combination of the above digested into smaller pieces by enzymes.

For screening a single gene, one can use a PCR amplified region from genomic DNA, or from a cDNA, or from RNA, by using sequence-specific primers. Preferably, one uses a high fidelity polymerase (such as Clontech HF-2) to avoid polymerase-introduced mutations. The primers used to amplify the nucleic acid are preferably not phosphorylated at the 5' end, resulting in an amplified product with no 5' P ends, if one identifies mutations using the 5'P end. If one uses 3'OH for such identification, then the primer is designed to result in a product with no 3'OH ends. A second PCR reaction can be used to amplify a wild type target, to serve as the control nucleic acid. Preferably, the PCR product(s) is purified (for example, using Qiagen purification following gel electrophoresis).

For screening many genes simultaneously, the nucleic acid can be genomic DNA (or a fraction thereof), or complex, PCR-amplified regions of genomic DNA, or a cDNA library, or RNA. One can use any method to prepare the nucleic acid sample. The target and control DNA are digested with any restriction enzyme that cuts at specific four base pair recognition sequences without generating blunt ends, such as Sau3A. The control DNA sequence is preferably the wild type target DNA sequence. However, it can be any nucleic acid sequence that you want to compare with another. For example, one could use a nucleic acid sequence from someone having a genetically associated disorder such as colon cancer and compare that sequence with someone having, for example, a spontaneous colon cancer to identify changes relative to the two conditions. When polymorphisms (also known as SNPs) between two alleles of a single individual are examined, one allele is taken as the 'target' and the other allele is taken as the 'wild type.'

When screening many genes simultaneously, double stranded linkers are ligated on to both ends of each fragment. The linkers are double stranded synthetic complementary oligonucleotides 16-30 basepairs (bp) long, designed so that they form either blunt ends or 'sticky ends' (i.e. ends with an overhang) complementary to the sticky ends of the DNA. These linkers are synthesized so that they do not contain 5' phosphate groups at their ends. Each fragment can then be amplified by PCR, using a synthetic primer complementary to the ligated linker. A single primer can be used for PCR because a single linker has been added to both ends of each fragment. The resulting PCR products are simpler representatives of the target and control DNA. Because these fragments are newly synthesized, they do not contain damaged bases (e.g. oxoguanines or uracils) which may have been present in the starting nucleic acid preparation. In an alternative embodiment, for genome-wide screening, amplification by PCR need not be used.

The control nucleic acid can be a wild type fraction similar to the target. This wild type likely will have no mutations. The control nucleic acid can be selected depending upon the intent of the test. For example, where acquired mutations in cancer cells are being screened, the control nucleic acid can come from a "normal" cell from the same individual. In other instances, for example, where an inherited (genetic) component may be involved, the control DNA would come from a different subject than the individual the nucleic acid; or simply differences among the paternal and maternal alleles can be examined by a self-hybridization of the DNA of the examined individual.

Step 2: Heteroduplex Formation

To create mismatches, the target nucleic acid is mixed and hybridized with wild type nucleic acid to form heteroduplexes, which will contain mismatches at the positions of difference between the target and control nucleic acid. Such mismatches can include polymorphisms, mutations, and other changes that result in such differences. For example, methylation. For example, loops and/or single stranded regions of one or more nucleotides occur at sites of deletions/insertions.

Heteroduplex formation typically involves denaturing the target and control nucleic acid, for example by heating, followed by renaturing under conditions (such as temperature) which allow hybridization to occur. For example, the target and control DNAs can be denatured at 95° C., then incubated overnight (i.e. 6-18 hours) at 60-65° C. Preferably, 5 mM hydroxylamine is included to reduce undesirable heat-generated strand breaks. Heteroduplex formation can also be achieved using, for example, phenol-emulsion hybridization. For multi-gene screening (such as genome screening), the phenol-emulsion hybridization method is preferred.

Step 3: Removal of 5' Phosphate Groups

To ensure the absence of any 5' phosphate groups, the heteroduplexes are dephosphorylated. A preferred method is treatment with calf intestine phosphatase (CIP). Following dephosphorylation, standard nucleic acid purification procedures (such as Qiagen filters) can be used to remove the CIP. Alternatively, 3' hydroxyl groups can be removed by known techniques.

Step 4: Cleavage at Mismatch Sites

Any agent that cleaves the target DNA at sites of mismatches can be used, thus generating strand breaks at sites of alterations due to polymorphisms, mutations, and/or methylation. Preferred agents include chemical compounds, enzymes, or combinations thereof Preferably, the agent generates strand breaks with a 5' phosphate group or a 3' hydroxyl. More preferably, the agent generates strand breaks with a 5' phosphate group.

Examples of chemical compounds that can be used include but are not limited to hydroxylamine, osmium tetroxide, potassium permanganate, tetraethyl ammonium acetate, hydrazine, and carbodiimide, which bind covalently to unpaired DNA bases such as cytosine or thymidine. These cleavage sites can then be converted to 5'P containing strand breaks via a standard treatment with piperidine. Other chemical compounds are DNA intercalators which bind preferentially to mismatches, and upon photoactivation produce a 5'P-containing strand break (e.g. bis(2,2'-bipyridyl) (5,6-chrysenequinone diimine) rhodium(III)).

Examples of enzymes which recognize mismatches and cleave at the site of mismatch include but are not limited to glycosylases, resolvases, cleavases, ribonucleases, and nucleases. Glycosylases, such as MutY or TDG, or their human homologues, excise a mismatched base, leaving an apurinic site. This site is then converted to a 5'P containing strand break via simple alkali or heat treatment, or via treatment with another enzyme which recognizes abasic sites and cleaves the strand (e.g. endonuclease III, or FPG glycosylase, or endonucleases, etc). In particular, if a 5'P-endonuclease is used, treatment with an additional enzyme—known as de-RPase—may be used to clean 5'P on the cleaved strand. Resolvases which can be used include T4 endonuclease E7 (T4E7), T7 endonuclease E1 (T7E1), E.coli endonuclease V, and CEL-I endonuclease, which cleave mismatches and loops in DNA. Cleavase cleaves DNA loops. Ribonucleases which cleave DNA:RNA hybrids can be used, for example when the 'target' is DNA and the 'control' is RNA. Nucleases such as S1 which have a preference for cutting single stranded DNA regions can also be used. A combined chemical-enzymatic method may also be used to cleave the target at sites of mismatch. This method comprises (i) treating the DNA with sodium bisulfite under conditions such that only unpaired cytosines are converted to uracils (e.g. mismatched cytosines or cytosines in a single strand formation); (ii) treating the DNA with single strand specific uracil glycosylase (e.g. human uracil glycosylase; or single-strand-specific uracil glycosylase), thereby creating abasic sites at positions of uracils; and (iii) creating a 5'P at the position of uracils via one of the methods outlined above. In one embodiment, one can use restriction enzymes and determine the difference in cuts between the wild type and the sample being tested.

The nucleic acid fragment(s) which has been cleaved at the site of mismatch is sometimes referred to as the "modified fragment."

Step 5: Second strand synthesis of a change occurs generating a new site a different number of cuts will occur. In a preferred embodiment one identifies restriction enzymes that will not ordinarily cut the wild type segment. If a mutation occurs creating a new site that is recognized by the enzyme, it can readily be detected.

To separate the two strands of the heteroduplex, only one of which has typically been cleaved at mismatch site, the nucleic acid is denatured to generate single stranded fragments. Denaturation can be via temperature, for example by heating the sample to 95° C. for 3-30 minutes.

The synthesis of the second strand is accomplished using standard synthesis techniques, such as primers and polymerases. To synthesize the second strand for each member of the heteroduplex, the sample is split into two equal portions, to allow a strand-specific primer to be added to separate reactions. The resulting double stranded DNA fragments are non-phosphorylated except for the fragment which contained the mismatch and was cleaved. The modified fragment will have a blunt-end with a 5' P, or a 'sticky' end with one or more bases overhanging the 3' end as well as a 5' P end, as certain polymerases sometimes add an extra adenine, or other bases, at the end of the synthesized strand.

Any polymerase which can synthesize the desired nucleic acid may be used. Preferred polymerases include but are not limited to Sequenase, Vent, and Taq polymerase.

For second strand synthesis when the target is a single known gene, the primers can be the same as those used to initially amplify the target, as described in step 1 above.

For second strand synthesis when the target nucleic acid includes many genes (such as a genome), the primer is the same primer used to amplify the original fragments before heteroduplex formation, as described above.

Step 6: Ligate Linker at Cleavage Site

To label each modified fragment, a unidirectional linker is ligated at the 5' phosphate group at the position of the alteration. The two members of the heteroduplex are maintained as separate samples following their separation and second strand synthesis, as described in step 6 above. The linker can be formed by annealing two asymmetric, complementary oligonucleotides (e.g. a 24mer and a 12mer) which anneal to form a blunt end, with no overhanging bases. Alternatively, the two asymmetric, complementary oligonucleotides can anneal to have some bases protruding at one end (i.e. a sticky end); the protruding bases(s) for example can be thymidines. In another preferred embodiment, both a blunt end and a sticky end linker can be used. The linker can be ligated to the modified fragment using standard conditions, such as an excess of T4 DNA ligase, incubated overnight (6-18 hours) at 4-15° C. Ligation is typically followed by purification of each sample, e.g. using Qiagen, to remove unligated oligonucleotides, enzymes, and small molecules.

In one embodiment, the linker can contain a detectable marker such as biotin. A biotinylated linker is preferably used when screening many genes simultaneously, such as genome-wide screening.

Step 7: PCR Amplification of Modified Targets

PCR is used to amplify the modified target nucleic acid(s). One of the primers is complementary to the ligated linker; thus, only those nucleic acids which were modified are recognized by this primer. The second primer is the same second primer used for second strand synthesis, as described in step 5 above. Any method of nucleic acid detection can be used to detect the final products. For example, gel electrophoresis.

For PCR amplification of modified target nucleic acids when screening many genes simultaneously, the biotinylated linker can be used to separate the modified target molecules from the unmodified molecules. More particularly, the sample is contacted with a streptavidin solid support (e.g. magnetic microspheres) to isolate biotinylated DNA fragments. PCR is performed on the isolated DNA, for example the microspheres. One of the primers is complementary to the linker ligated at sites of mismatch, as for the single gene method; the other primer is complementary to universal linker used to initially amplify all fragments as well as for second stand synthesis.

PREFERRED EMBODIMENTS OF THE INVENTION

Eliminating Second Strand Synthesis

It is possible to circumvent step 5 if the enzyme(s) used in step 4 can cut both DNA strands (generating double strand breaks) at the position of the mismatch. Examples of enzymes that can generate double strand breaks include the resolvases (for example, T4 endonuclease E7 (T4E7), T7 endonuclease E1 (T7E1), Ecoli endonuclease V, and CEL-I endonuclease). The resulting 'sticky' DNA end can be converted to a blunt, 5' P-containing DNA end via the use of exonuclease. Ligation of a blunt-end unidirectional linker, as in step 6, follows without the need for denaturation and second strand synthesis.

Double strand breaks can also be created by using an enzyme (as described in step 4) which generates a single strand break, followed by treatment with an enzyme (e.g. S1 nuclease) that will nick the strand opposite to the mismatch, thus creating a cut on both DNA strands. Also, instead of an immediate S1 nuclease treatment, an exonuclease III treatment can be applied. Exo-III will initiate degradation of one strand at the position of the DNA nick, and will generate a single-stranded region (e.g. 100 base pairs long) in the double stranded DNA template. The single stranded region is then preferentially nicked by S1, thus generating DNA molecules with double stranded cuts.

Use of Restriction Enzymes to Generate Double Strand Breaks at Mutations

In another preferred embodiment, restriction enzymes may be used in Step 4 to cleave the target DNA at sites which contain polymorphisms or mutations, thus generating double strand breaks. This preferred embodiment relies on the presence of a mutation which generates a novel restriction enzyme recognition site in the mutant allele that is not present in the cannol, wild type allele. Thus, only mutant DNAs, which contain the recognition site, are cleaved by the restriction enzyme.

Any restriction enzyme may be used. One identifies additional cuts that occur versus the original. Preferably, the enzyme does not cleave the wild type DNA, thus one can readily identify if it does cleave the non-wild type. As used herein, restriction enzymes are sometimes referred to as restriction endonucleases. Preferred enzymes include four-base cutter enzymes that recognize sites comprising four nucleotides, including but not limited to N1AIII, SA43A1, TagI, MaeII, MaeI and MseI.

In this restriction enzyme-based embodiment, heteroduplex formation (Step 2) is not required because the cleavage method does not require the presence of a mismatch. Other steps of the method are as described above.

Figure 7:
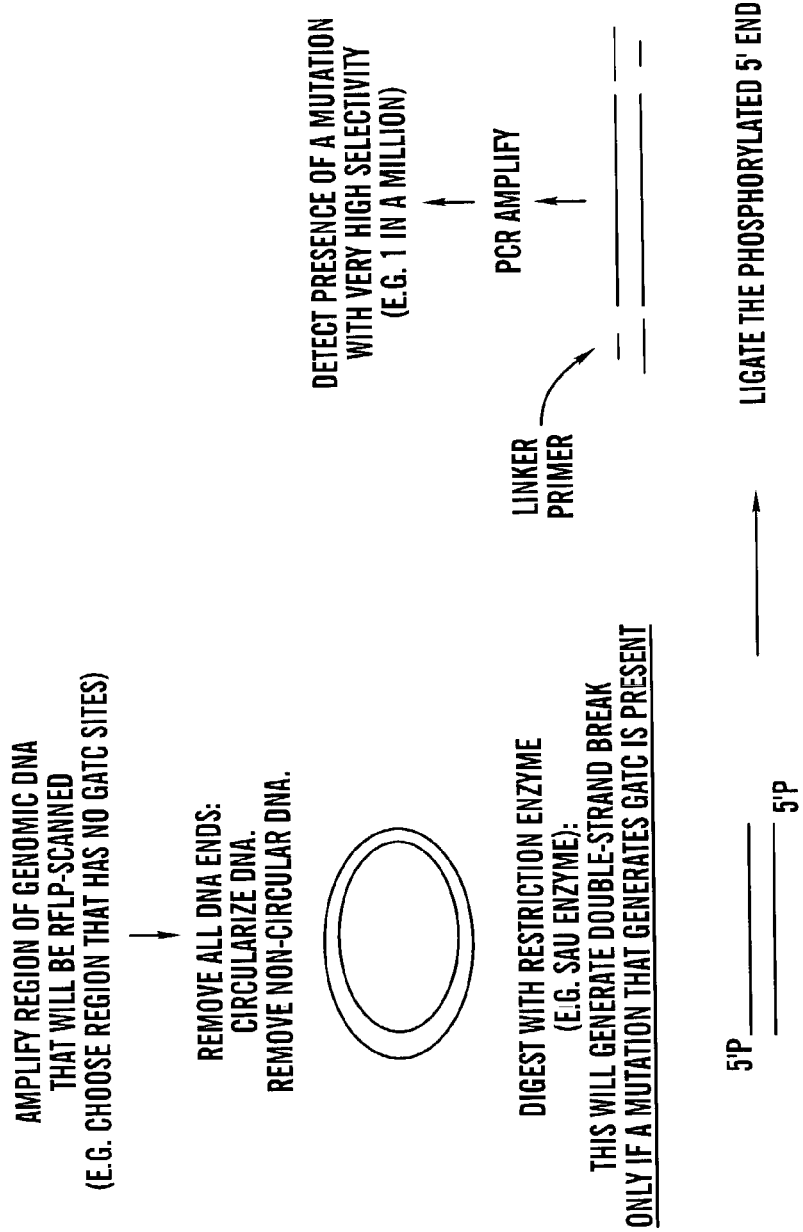
FIG. 7 shows a schematic of a variation in the present technology for screening for mutations in a single gene. In this variation, a restriction enzyme is used to detect mutations which generate a recognition sequence for the restriction enzyme which is not present in the wild-type allele. This variation also uses circularization of the DNA prior to restriction enzyme cleavage at sites of mutation to allow very high selectivity for mutation detection.
Figure 8:
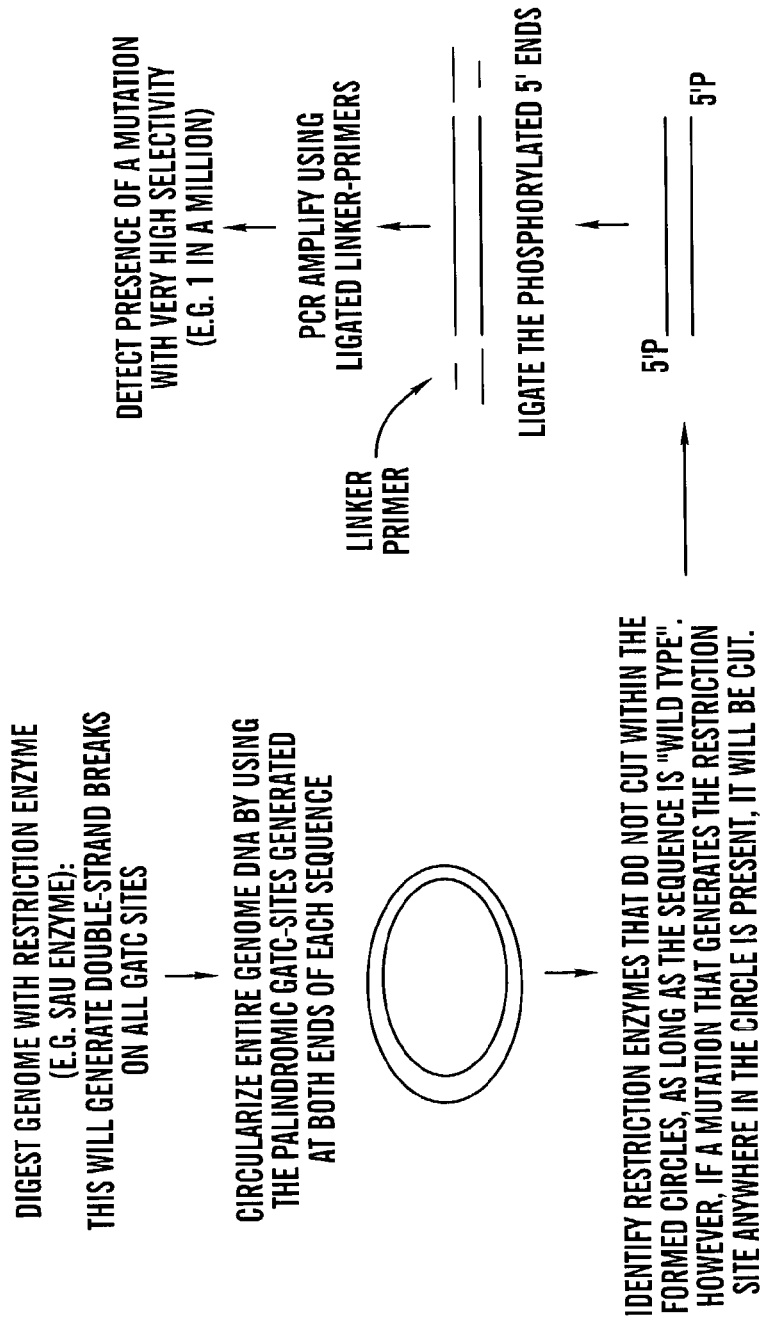
FIG. 8 shows a schematic of a variation in the present technology in which restriction enzyme cleavage and DNA circularization are combined to allow scanning for mutations in a whole genome.

Modifications described herein to the basic method may be combined with the restriction enzyme-based embodiment. One further preferred embodiment includes combination of the restriction enzyme method with the circularization method described below. This combined approach is depicted in FIG. 7, to-detect mutations in a single gene, and FIG. 8, to detect mutations in a whole genome.

Methylation Detection

In another preferred embodiment, the method of the present invention can be used to detect whether methylation has occurred in a sample, such as single known gene or multiple genes. The methylation detection method preferably uses genomic DNA to assay the degree of methylation. No heteroduplexes are formed, and steps 1-3 of the above-described method are omitted.

The methylation detection method comprises a chemical or enzymatic approach for methylation-sensitive treatment of genomic DNA. Chemical treatments include the incubation of genomic DNA with sodium bisulfite, which selectively and completely converts non-methylated cytosines to uracils. The DNA is first heat-denatured and then treated with 5M bisulfite, pH 5-7. Following this, uracil glycosylase is used to convert uracils to abasic sites, which are then converted to 5'P-containing strand breaks via heat or alkali, as described above. Pretreatment of genomic DNA to remove pre-existing uracils is used prior to bisulfite treatment. This pretreatment consists of uracil glycosylase treatment in the presence of 5 mM hydroxylamine, pH 7.

Enzymatic approaches that can be used to convert methylated cytosines to 5'P include treating genomic DNA with 5-methyl-cytosine glycosylase, which removes the methylated cytosines, leaving an abasic site, which is then converted to 5'P-containing strand break as described. Another enzymatic approach is to use methylation-sensitive restriction endonucleases, which only cut non-methylated sequences, producing directly 2 5'P—one on each strand.

Steps 5-8 described in the above-described method are then followed, to synthesize a second strand directly in the genomic DNA sequence of interest. The primers used to synthesize the second strand must be specific, to avoid priming of other genomic regions. If bisulfite is used as a treatment, the actual sequence which is targeted by the primer will have changed since cytosines become uracils. Therefore the design of the primer must take this into account for adequate priming of the targeted region, i.e. guanines must become adenines in the primer design. Following this, a linker is ligated to the unique 5'P ends, and then PCR takes place.

The result of the PCR is a product whose amount is proportional to the degree of methylation (or non-methylation, depending on the method selected in Step 1) of the target sequence. The product consists of a range of sizes of DNA, starting at the primer and finishing at the positions of cutting, i.e. the positions of methylation (or non-methylation). This product is run on a sequencing gel to identify the positions that were cut at a nucleotide resolution.

The method for detecting methylation can also be applied to screen many genes simultaneously, such as a whole genome.

The control genome can be normal tissue and the target genome can be cancer tissue from the same individual. The desired quantity here is the genome-wide differences in methylation, as methylation has been associated with causing cancer and other diseases.

To screen a whole genome, the genome is digested with a restriction enzyme, linkers are added and a methylation-sensitive treatment takes place. No PCR is performed as PCR would eliminate all of the methylated cytosines which are to be detected. The remaining steps are the same as with the mutation screening, as described above and below. The net result will be two samples (one from cancer cells and one from normal tissue cells) differentially enriched in methylation sequences in specific genes. To identify which genes are differentially methylated in the two samples, known approaches can be used. For example, subtractive hybridization between the cancerous and normal tissue PCR products can isolate those genes that are differentially methylated in the two populations, and the genes can then be identified using standard methods (i.e. microarrays, sequencing, cloning, etc).

One can also screen for sites other than methylation by adapting the above method and identifying alterations associated with a particular change.

Circularization of DNA Fragments to Remove All DNA Ends and Mis-hybridizations

Figure 3:
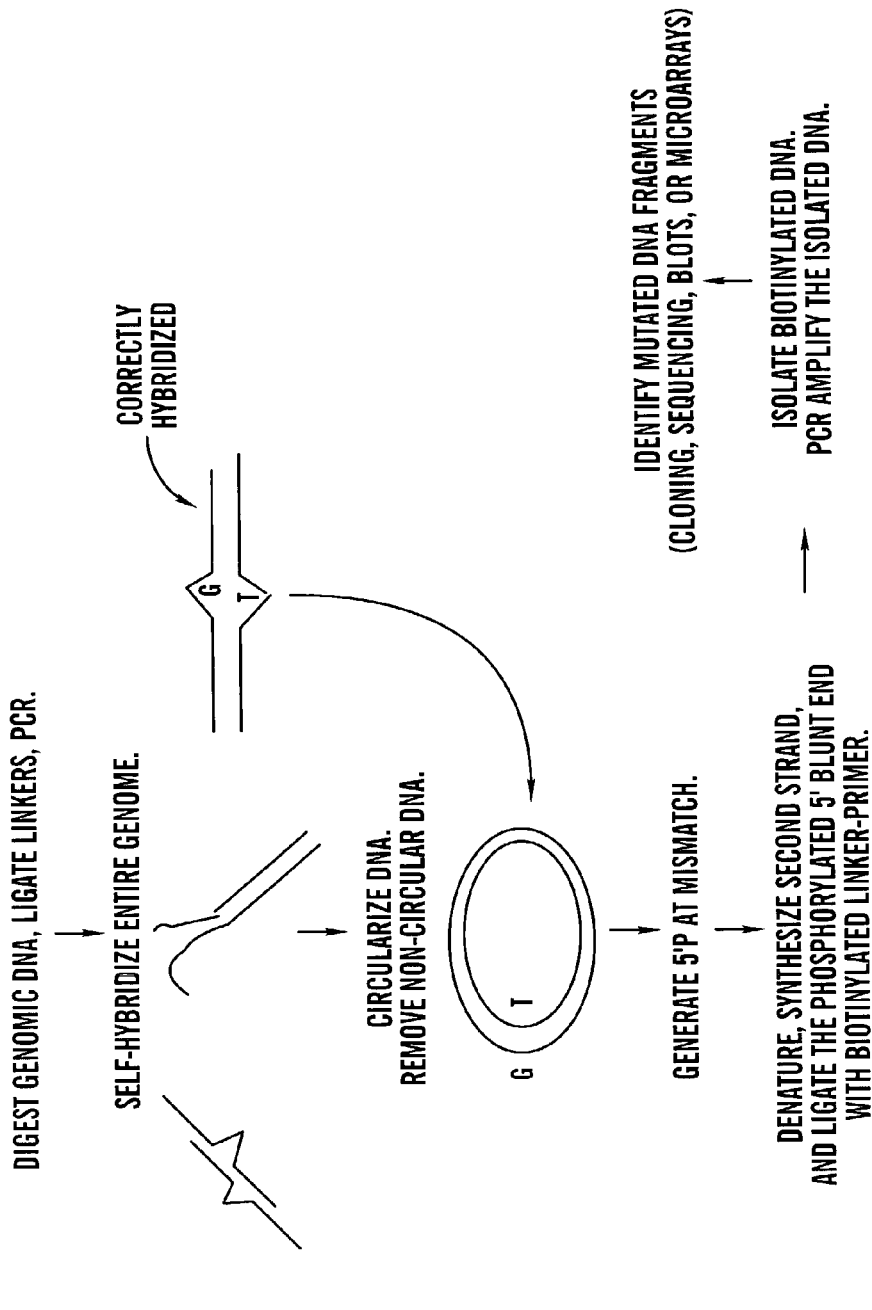
FIG. 3 shows a schematic of a variation of the present technology to screen for mutations in genomic DNA, in which the DNA is circularized prior to cleavage at mismatch sites to remove DNA ends and mishybridizations.

To enhance the elimination of every unwanted 5'P DNA-end from the nucleic acid prior to generating unique 5'P ends on the mutation-containing fragments of the genome, the nucleic acid can be circularized following heteroduplex formation (step 2), before cleavage at sites of mismatch (step 4). This preferred embodiment is illustrated in FIG. 3 and involves the following modifications.

Step 2: The longer of the two linkers is 5'-phosphorylated. This is done either by using an ab initio phosphorylated linker or by phosphorylating the linker after ligation, by using T4 polynucleotide kinase in a standard reaction. By using this linker, a 5'phosphorylated 'sticky' end is introduced at the end of each DNA fragment. Similarly, the shorter of the two linkers added in step 2 is 3'-phosphorylated, so that upon ligation to DNA both linkers are ligated with covalent bonds. The sequence of the linkers is such that, after ligation, the 'sticky end' of the DNA is a palindromic sequence (e.g. a GATC, or GATATC, etc).

Step 3: The (optional) PCR in step 1 may or may not applied here. If it is not applied, then one proceeds directly to circularization step (see below). If however the DNA is PCR amplified, the 5'end of the DNA will not contain a phosphate group. To phosphorylate the 5' end, a high fidelity polymerase with terminal transferase activity is used (e.g. Clontech HF-2) in order to add an extra adenine at the end of each product. The 5' end of DNA is then phosphorylated using T4 polynucleotide kinase.

Circularization Step:

The DNA is circularized by self-ligation of the complementary, palindromic sequence sticky ends with 5'P. Self-ligation is a well-known reaction that occurs by reducing the DNA concentration and adding excess T4 DNA ligase in an overnight reaction. The only DNA fragments that will be successfully circularized are those that hybridized correctly, as both ends of the DNA must be perfectly matched for re-ligation to occur. In addition, the circularized fragments will contain no ends, (i.e. no 5'P or 3' OH will be present in the circularized DNA). Treatment with exonuclease III and/or S1 nuclease or other nucleases will remove any DNA fragments that are not circularized.

The circularization approach comprises a general method to remove all possible ends from DNA, including the 5'P, 5'OH, 3'P or 3'OH ends. As a result, this strategy allows not only the removal of 5'P, but also of any other 'ligatable' DNA end, such as the 3' OH. In particular, another enhancement of this embodiment is described below.

The circularization embodiment can also be combined with rolling circle amplification, following selective degradation of one of the two strands of circularized DNA. This preferred embodiment generates single stranded DNA circles prior to amplification (steps 5-7), allowing increased detectability of the alteration.

The following modifications can be used to detect and amplify those circularized DNA fragments that contain mismatches using rolling circle amplification.

Step 4: Following circularization as described above, treat with an agent that generates a strand break (nick) at the position of the mismatch, or very close to it. Such agents are those described in step 4. Next, treat with exonuclease III that initiates digestion of one strand of the circularized DNA, starting at the position of the nick. The result is that DNA circles that contain a mismatch will be converted to single stranded DNA circles.

Step 5: Second strand synthesis can be initiated selectively at the single stranded DNA circles. Synthesis of the second strand is performed using a DNA polymerase with strand-displacement properties, like the one used in the technique known as 'Rolling Circle Amplification' (4). In this process, the polymerase will perform a full 'circle' synthesizing DNA complementary to the single-strand containing circles. When it completes the first circle it will encounter the 5' end of the primer and will start displacing the first circle, synthesizing a second circle, then a third circle, etc. After several rounds the polymerase will stop the synthesis. The result is that a long, single strand of DNA will emerge out of each single stranded circle, i.e. out of DNA that originally contained mismatches.

Figure 4:
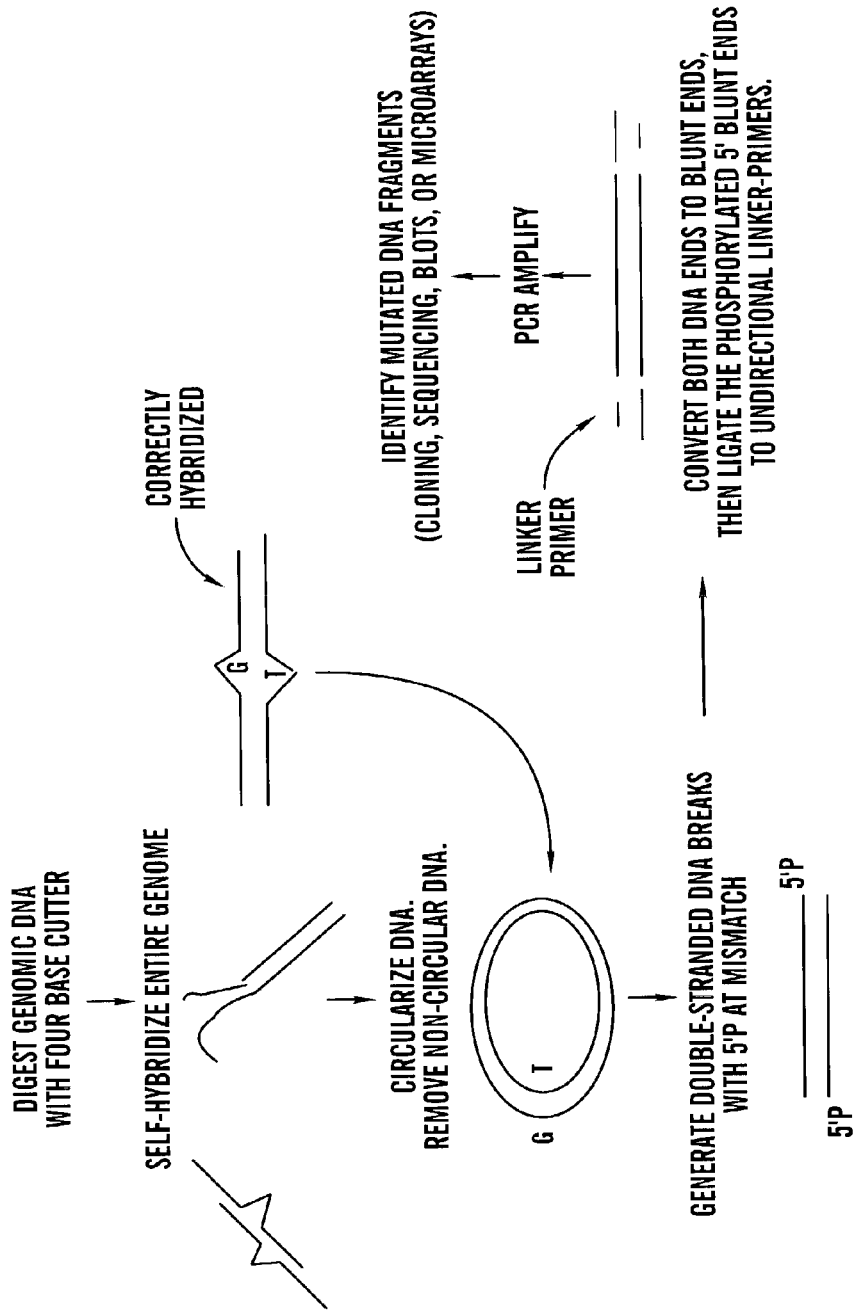
FIG. 4 shows a schematic of a simplified variation of the present technology, in which the enzyme used to generate the 5' P cuts both DNA strands at the position of the mismatch.

The circularization embodiment can also be combined with approaches that introduce double strand breaks, thus eliminating the requirement for second strand synthesis and for biotinylated primers (FIG. 4). It is possible to reduce several of steps if the enzyme(s) used to generate 5'P can cut both DNA strands at the position of the mismatch, which in effect combines the steps.

The steps of a preferred simplified embodiment of the present invention are as follows (FIG. 4):

Step 1: Digest genomic DNA with a four base cutter enzyme that creates sticky ends.

(optionally, the DNA can be ligated and PCR amplified as in step 1 above).

Step 2: Self-hybridize the entire genome, to create mismatches/loops at positions of mutations.

Step 3: Circularize DNA (only correctly hybridized DNA will circularize successfully).

Step 4: Remove enzymatically non-circular DNA (e.g. exonuclease treatment).

Step 5: Generate 5'P (or 3'OH)-containing DNA breaks at the mismatch position, on both of the DNA strands.

Step 6: Make blunt ended, 5'P (or 3'OH) containing -DNA by use of exonuclease.

Step 7: Ligate linker primers on both ends of the 5'P-containing (or 3'OH-containing) DNA. PCR amplify.

All DNA fragments with mutations are selectively amplified (Genome-wide mutation screening). This simplified approach provides a powerful application of the present invention, as it allows genome-wide mutation scanning in a very simple protocol.

Use of 3'OH DNA Ends Plus Circularization to Attach a PCR-able Linker-primer

In another preferred embodiment, all 3'OH ends are removed from DNA, prior to creating unique 3'OH at the positions of alteration. Next, a phosphorylated primer is ligated to the 3'OH and the scheme described above is repeated. Therefore instead of using 5'P-ends to ligate a PCR primer at the position of alterations, as described above, another DNA end, the 3'OH, is used to achieve PCR amplification of mutations/methylation. More specifically, this embodiment uses the methods described above to first remove all DNA ends (whether these contain 5'P or whether they contain 3'OH or other chemical group). Following this, the following modifications are used:

A chemical or enzymatic method is used to generate, directly or indirectly, 3'OH at the positions of mutations in the circularized DNA. Most of the chemical and enzymatic approaches used to make 5'P in step 4 will also generate a 3'OH DNA-end and can be used for this purpose.

Following that, an enzyme (e.g. terminal deoxynucleotide transferase) is used to add successive guanines to the 3'OH end (a process known as ribonucleotide tailing). As a result, all DNA ends now contain a known, common sequence (e.g. GGGGGG) and a common method to ligate a PCR primer (known as sticky-end ligation) at this end can be employed.

Apart from the fact that the PCR primer is ligated to unique 3'OH groups, instead of 5'P, all other steps are the same as those described above.

Use of DNA Polymerase Plus Pyrophosphate to Generate Unique, Ligatable 5'P or 3'OH Ends in DNA Another novel approach that can be followed to generate unique 3'OH or 5'P at the positions of mutations, which can then be ligated to a primer, is by using a lesser-known property of DNA polymerase, known as *pyrophosphorolysis* (e.g. T4 DNA polymerase, human DNA polymerase, etc). The usual function of polymerase is to polymerize a new DNA strand opposite an already existing strand, by utilizing deoxynucleotide triphosphates (dNTPs). Following addition of dNTPs to the new strand, the polymerase reaction generates pyrophosphate. However, DNA polymerase will also perform the opposite action in a double stranded DNA ('pyrophosphorylation'). By supplying excess pyrophosphate in the absence of dNTPs, it will de-polymerize one of the strands of the double stranded DNA starting from the 3' end, by removing dNTPs in a reverse enzymatic reaction. In a perfectly matched double stranded DNA template this pyrophosphorylation reaction will proceed simultaneously from both 3'OH ends of DNA by removing dNTPs one by one. Following each dNTP removal, a newly created 3'OH is generated on the degraded strand. In the presence of a mismatch along the double stranded DNA structure, the pyrophosphorolysis will stop. The present invention takes advantage of this phenomena in order to ligate a PCR primer at the position of mismatch. This is done with the following modifications to the protocol described above:

In step 1, the linkers that are ligated are phosphorylated in such a manner that, after the ligation both linkers are covalently ligated to the DNA (for this purpose the synthesized shorter linker needs to be 5'-phosphorylated). In addition, the 3'OH end of the shorter linker is made to contain a di-deoxynucleotide instead of a deoxynucleotide (this prevents addition of nucleotides to the 3' end by terminal transferase, which will be used in latter steps). Finally, some of the shorter linkers that are added (e.g. 50% of the total) are made such that they form DNA mismatches with the longer linker in the last few bases towards their 3' end. (This prevents DNA polymerase from initiating the pyrophosphorylation reaction from that 3'end, and hence will not degrade DNA starting from this strand. Other 'blocks' for the pyrosphosphorylation reaction can also be inserted during the synthesis of this short linker, e.g. insertion of an abasic site, or a modified nucleotide not recognizable by polymerase). As a result, 50% of all DNA molecules will contain on one of their ends a degradable substrate for pyrophosphorolysis (i.e. a common, perfectly matched, 3'OH) and on the other end a non-degradable substrate.

The (optional) PCR in step 1 is omitted here. Following hybridization as described in step 2, mismatches are formed internally in DNA, due to mutations. The pyrophosphorylation reaction is then initiated: DNA polymerase degrades one of the two DNA strands, starting from the 3'OH ends of the added linkers. For DNA fragments that carry linkers that contain perfectly matched 3'OH on both their ends, the mismatch degradation will occur from both sides of the DNA fragment. For DNA fragments that contain pyrophosphorylation 'blocks' on both ends, no degradation will occur. Finally, for DNA fragments containing pyrophosphorylation 'blocks' on one end only, degradation will proceed from only one of the two ends. In this case, if (and only if) a mutation—caused mismatch is encountered by the polymerase, pyrophosphorylation will stop, and a unique 3'OH end will remain on one strand. (It should be noted that no other 3'OH is present in the entire sample at this point since the 3'OH originally present degraded by pyrophosphorylation).

This unique 3'OH DNA end can be used for ligation in one of two ways: Either by using the enhancement protocol employing double strand breaks, which utilizes addition of a biotinylated linker—primer via terminal deoxynucleotide transferase (TdT) plus ligase, or by utilizing exonuclease to degrade from the 5' end the DNA strand opposite to the strand degraded by pyrophophorolysis, until the position complementary to the unique 3'OH. A blunt DNA end containing 5'P will thus be created. This can be directly ligated to the unique, biotinylated linker—primer as described in step 6. Step 7 is then applied to amplify only the DNA fragments that have mutations.

'In-Situ' Mutation Screening in Genomic DNA

This embodiment is an intermediate approach, which can be used to detect mutations in genomic DNA. Screening is not performed in all genes simultaneously, but only to a number of specific genes that the user is interested in (e.g. at least 5 genes, more preferably at least 10 genes, still more preferably at least 25 genes, even more preferably at least 50 genes. Yet more preferably at least 75 genes are screened. Even more preferably at least 100 genes. For example 100-1000 genes). For several users, scanning for 100-1000 genes will serve the purpose.

Using the protocols described in the embodiments above, in this approach the genomic DNA is:

Digested with a restriction enzyme (e.g. a four base cutter) to generate DNA fragments of smaller size.

Ligated with linkers which can subsequently serve as PCR primers.

Mixed with a large pool of double stranded PCR products of a high concentration (e.g. 1 µM). Each PCR product has been generated from a 'standard genomic DNA' whose exact sequence is known a-priori. For examining a specific number of regions, e.g., 100 regions in the unknown genomic DNA, 100 different PCR products need to be simultaneously mixed. The PCR products can be variable in length, but preferably in the region 100-1000 bp each. All PCR products are amplified from the original standard genomic DNA so that they contain a common sequence at both their ends, which preferably has no complementarity with human genomic DNA (e.g. the M13 sequence TGT AAA ACG ACG GCC (forward primer) and AGG AAA CAG CTA TGA CCA T (reverse primer).

Denatured at 95° C. for 5 minutes, and then incubated for 3 hours at 65-80° C. to allow the pool of PCR products to hybridize to their complementary sequences on the unknown genomic DNA. If there are alterations in the unknown genomic DNA, then mismatches or loops will be formed between the PCR products and the genomic DNA regions, following hybridization.

The steps 5-7 described above are then used in order to generate unique 5'P or 3'OH ends in the genomic DNA regions that have hybridized to the PCR products. These are then uniquely ligated to a linker—primer and selectively PCR—amplified as described above.

The result is that all alterations, which are potentially mutations, present within the regions addressed by the PCR products will be simultaneously isolated.

Sources of Mutations/Polymorphisms/Other Sites Such as Methylation Sites

The present method recognizes mismatches formed upon hybridization of the target DNA and the control (e.g., wild type) DNA. Those skilled in the art are aware that mismatches may appear as a result of inherited or acquired genetic alterations. Also, that not every mismatch is the result of mutation but that some mismatches simply represent polymorphisms that occur naturally in populations. Both the inherited and the acquired genetic alterations in DNA will cause a mismatch.

Furthermore, those skilled in the art are aware that because all eukaryotic cells contain two copies of each chromosome, one paternal and one maternal, differences between the two alleles of each gene may also cause mismatches. In this case one gene copy (e.g. the paternal) will act as a control DNA and the second gene copy (the maternal) will act as the target DNA, and the mismatches will form upon hybridization of maternal and paternal DNA (i.e. simply by self-hybridization of DNA present in cells). These inherited differences can represent either polymorphisms or mutations.

There are a number of ways known in the art to distinguish whether a particular mismatch is an inherited polymorphism or mutation, or an acquired mutation or yet some other site.

One method that can be used to identify acquired mutations is to have the control DNA come from the same individual. For example, when screening a malignant cell the control DNA can be obtained from the corresponding non-malignant cell. By screening first the non-malignant cell alone and then the malignant cell (or a mixture of malignant and non-malignant cells) a comparison of detected mismatches in the two cases can be made. Differences that appear solely on the malignant cell and not on the normal cell comprise acquired mutations which may have lead to the malignancy.

When inherited (genetic) mutations/polymorphisms (i.e. where the alteration from the wild-type is present at birth and in every cell of the body) need to be identified, only normal cells need to be examined. As explained, inherited differences between the two alleles will cause mismatches upon self-hybridization. Detection of these mismatches will indicate the positions of inherited polymorphisms or mutations. Thereafter, one standard method to discriminate inherited polymorphisms from inherited mutations is to screen kindred and to determine whether or not the mismatch is present in normal kindred (i.e. a benign polymorphism) or only present in kindred showing a particular abnormality (i.e. a debilitating mutation).

The use of databases categorizing mutations and polymorphisms has also been increasingly popular. Thus, comparison of an identified genetic variation with those contained in a database can in many instances be used to determine whether the detected mismatch in DNA is due to a mutation or due to a polymorphism. One can also look at whether the mismatch causes truncation in the expressed protein.

Finally, another method that can be used to discriminate among mutations and polymorphisms is by the use of in-vivo assays. Thus, one can substitute a gene with at least one engineered base substitution mutation for the wild type gene in an assay to determine whether or not the gene with the mutation can functionally replace a wild-type normal gene. If a gene can replace a wild type normal gene in an assay and exhibit almost normal function that gene is not considered a mutation, but an allelic variation (i.e. polymorphism). If it cannot that gene will be considered a mutation.

One of the advantages of the present approach as opposed to mutation-detection methods presently being used is the ability to identify numerous mutations at diverse places in the genome. This permits one to determine if certain genes not presently associated with a particular abnormality may also have some relationship with that abnormality. For example, with hereditary non-polyposis colorectal cancer (HNPCC), mutations in the MSH2 and MLH1 genes are believed to be responsible for approximately 90% of the cases. A number of other genes have been identified as being responsible for the other 10% of the cases. However, in view of the cost of screening one typically looks primarily at MSH2 and MLH1. It may turn out when an array of genes are looked at the same time, that mutations in other genes also play a major role, in an individual with a particular condition. These other mutations may be associated with severity of the condition. By monitoring these additional genes and looking at disease state and recovery, one can develop a better idea of prognosis and treatment regimes than is currently available.

When using genomic DNA the skilled artisan is aware that numerous mismatches can and will occur in non-coding genetic regions. Looking at non-coding regions can permit the identification of mutations that affect expression and levels of expression. On the other hand when one is interested in looking for mutations in the expressed proteins it is preferable to use the mRNA to generate cDNA, and then form mismatches that can be detected by the present approach.

The present method allows for extremely sensitive mismatch—scanning in diverse DNA fragments, thereby resulting in sensitive and high throughput mutation screening over several hundreds or thousands of genes at once. For example, it becomes possible for the screening and discovery of novel mutations in tumor samples which is instrumental to establish the pathogenesis of cancer and to establish new relations between mutations and cancer or other diseases. The new compounds and methods described above are also useful in analysis of the genetic background (polymorphisms, mutations) of any individual. High throughput genotyping and genotypic selection can be carried out by the present method.

Mutation—Scanning Arrays

Using the present invention, a PCR product is generated which contains only those DNA fragments that contain mutations, while all other fragments are effectively eliminated by the procedure. However, the identity (e.g. gene of origin) of these mutated DNA fragments is still unknown, and the user still requires a method to identify where each mutated fragment belongs in the genome.

Several methods can be employed for this purpose (e.g. cloning, sequencing of selected PCR products from the isolated sample, Southern blotting, etc). One preferred method is by using DNA microarrays, also known as Mutation Scanning Arrays. The microarray allows the identification of presence or absence of every gene included on the microarray in the population of mutated DNA fragments produced by the current invention. For example, if a mutation is present on a 500 base pair—long fragment that lies towards the 5'-end of the BRCA1 gene, the array must contain a probe with a sequence complementary to these 500 base pairs so that it allows specific hybridization to occur when the DNA population is applied to the array.

Mutation on scanning arrays have been previously described (for example, U.S. Ser. No. 60/114,196, filed Dec. 30, 1998, and International Application No. PCT/US99/31177, filed Dec. 29, 1999; both applications are hereby incorporated by reference).

These mismatch-containing segments can be amplified by PCR and used, for example, in a DNA array to simply search for the matching gene in the array to identify which genes these mutation-containing fragments belong to. Consequently, existing arrays for multiplexed gene expression scanning such as known in the art can be used. For example, Affymetrix Hu6800 DNA Chip, or known arrays [Wodicka, L. et al, *Nature Biotechnology:* 15: 1359-1367 (1997); Lockart, D. J. et al, *Nature Biotechnology* 14: 1675-1680 (1996); Schena, M. *Trends Biotechical* 16:301-306 (1998): Yang, T. T. et al. *Biotechniques* 18: 498-503 (1995); Ginot F. *Human Mutation* 10: 1-10 (1997)]. Other arrays include the Telechem International Array (San Jose, Calif.); the Genetix Ltd. array (Dorset, UK); and the BioRobotics Ltd. array (Cambridge, UK). The chip such as the Affymetrix DNA chip contains densely packed DNA or RNA elements.

In order to increase resolution (i.e. definition of the gene segment containing the mutation/polymorphism) the fragment should be smaller. However, in order to effectively prepare large amounts of mismatch-containing fragments by standard techniques such as PCR, the fragments should be at least about 50 bases. In some instances for ease of operation, a loss in resolution can be tolerated and larger fragments used.

Preferably the mismatch-containing fragment is 50-300 bases, more preferably 50-200 bases, still more preferably 50-100 bases and most preferably about 50 bases.

The nucleotides on the array (gene elements) should be between 8-300 bases preferably no larger than the size of the DNA of the mismatch-containing fragments. For improved resolution, smaller sizes should be used. For example, 50 bases or less, more preferably 8-25 bases. Many arrays presently available use nucleotide fragments of about 25 bases. Typically, these nucleotide segments are selected to be close to the 3' portion of the transcript.

However, other DNA arrays as discussed, infra, can also be used. Such arrays, which contain fragments that span the whole length of the gene (i.e. from both the 5' end of the gene as well as the 3' end) are preferred.

Inherited single nucleotide polymorphisms (SNPs) and mutations can define a genetic predisposition towards several diseases, including cancer, cardiovascular, neurodegenerative and others. Indeed, acquired SNPs, mutations and loss of heterozygocity are particularly pertinent to cancer development, and early cancer detection. All of the above can be simultaneously detected by the above-described methodology.

For example, cDNA for tumor and normal tissue of a single individual is prepared. Because inherited polymorphisms is a frequent event (average 1 SNP per 1000 bases), several genes will have more than one SNP. Also, the tumor genes will contain one or more inherited SNPs as well as occasional acquired SNPs/mutations. Next, the cDNA for the tumor and normal tissue is subjected to the method of the present invention, to amplify fragments containing alterations.

The mismatch-containing PCR-amplified fragments are applied on an array such as the Affymetrix chip: Each mismatch-containing fragment will hybridize to its complementary oligonucleotide on the array, thereby revealing which gene and which gene region (to within 100-200 base pairs) the SNP/mutation belongs to. By comparing arrays from the tumor and normal tissue samples, both the inherited and the acquired SNPs/mutations can be derived. Loss of heterozygocity may occur when an acquired SNP/mutation occurs in the same gene with an inherited SNP/mutation. Such genes can readily be identified by comparing A and B.

A preferred Mutation Scanning Array should contain immobilized oligonucleotides, preferably 8-25 bases long, which span the whole mRNA sequence of each gene represented on the array, and not biased toward one or the other mRNA end. Rather they should cover the whole gene being studied. In some preferred instances, one uses genomic DNA to make the array and would use both coding, and non-coding portions. As mentioned, the oligonucleotides can be larger, but by increasing size, resolution is lost. The oligonucleotides should sample the mRNA in intervals not bigger than the DNA fragments isolated by present method preferably 50-100 bases but capable of ranging from 50-300 bases. In this manner the mismatch-containing fragment will be assured of finding a complementary sequence on the array. When immobilized oligonucleotides on the array are arranged to sample the mRNA at small intervals (e.g. 20 bases) there will be redundancy of information upon hybridization of the mutant fragments to the DNA chip, as each fragment may simultaneously hybridize to two or more immobilized oligonucleotides. In this case, by using the combined information from all array elements, a better resolution of the position of the mutation will be achieved.

The above-described modification will allow polymorphisms/mutation/methylation, etc. detection over the whole length of the immobilized genes to be identified. The immobilized genes can be either the whole genomic cDNA library, or an arbitrary fraction of that, or a specific collection of genes that are known to be related to a specific disease (i.e. disease specific arrays).

A major advantage of the present method is that it can detect polymorphisms such as SNPs/mutations in the presence of an excess of normal alleles in the initial sample because the methodology first isolates and amplifies the mutants, and the array subsequently identified the gene. This is currently impossible to do with existing technology.

The described technology can be used for mutation screening and for research. For example, the use of solid supports at every stage of the assay will substantially shorten the time required to screen tumor samples, improve its cost-effectiveness in terms of man-power as well as its reliability and reproducibility. An alternative mutation scanning array to the chip array is the use of beads, sometimes referred to as microbeads or microspheres. For instance, magnetic microsphere technology can be utilized to immobilize heteroduplexes at an early stage of the assay. Following mRNA extraction from e.g., a host cell such as cancerous and normal samples, cDNA for e.g. 588 genes can be generated. Thereafter PCR primers that contain a cleavable (S—S) biotin are added. Hybridization of the cancerous cDNA with wild-type alleles generates heteroduplexes at the positions of base substitution mutations, and the DNA sample is immobilized on, for example, the streptavidin-coated magnetic microspheres (available from Dynal Inc.). From this point onwards, all subsequent steps of the method of the present invention can be conducted on the solid support.

The microspheres allow chemical/enzymatic treatment of the immobilized DNA and efficient, rapid separation of chemicals from DNA via magnetic immobilization of the microspheres during washing.

Following removal of DNA samples from the magnetic microspheres, the samples will be applied on e.g. antifluorescein-microplates for PCR amplification and screened on the Clontech DNA hybridization array. Using the above procedures, base substitution mutations can be isolated, amplified by PCR and screened on the DNA array in less than 24 hours. Thus, this technique results in a standardized procedure with easy access to researchers and clinicians for cost-effective, large-scale mutation screening of a target sample, such as cancer samples.

See also U.S. Pat. Nos. 5,736,330 and 5,981,180 and the products of Luminex Corporation (Austin, Tex.). Flow cytometry can be used for diverse applications in hematology, oncology, cell biology, etc. Apart from cultured cells, beads (also known as 'microbeads', 'microspheres') tagged with fluorescent probes, or with biomolecules carrying fluorescent probes, are commonly used. During flow cytometry, such fluorescent microbeads are forced to flow down a thin tube and are individually excited by one or more laser beams. Light emitted from each microbead is then individually filtered and measured by an attached light detector. Depending on the signals obtained, individual microbeads can be separated (sorted) from the rest of the microbead population. Common flow cytometers can collect individual light signals and sort 10,000-30,000 microbeads per second. As a result, $10^8$ microbeads can be sorted in less than one hour. Specialized flow cytometers can count individual microbeads at much higher rates. Multiparametric flow cytometry allows each individual microbead to be excited by several lasers at once, and illumination by each laser produces optical emissions at several discrete wavelengths and intensities, depending also on the type and amount of fluorescently-labeled biomolecules bound to the microbeads. As a result, passage of each individual microbead through the flow cytometer can result to emission of a large set (5-7) of signals, which are individually detected and stored on a computer. The capability of rapidly sorting individual microbeads depending on the collected parallel optical signals makes flow cytometry a powerful tool for analyzing numerous genes in a very short period.

When a microbead tagged with a specific gene, it is also tagged with a combination of fluorescent probes it can be used in flow cytometry. The fluorescent probes with which the beads are tagged can have a variety of different fluorescent intensities. Consequently, for each bead there is a unique combination of intensities/fluorescent probes such that, passage of an individual bead through the flow cytometer uniquely identifies the immobilized gene. Further, if the gene immobilized on the bead has hybridized to a 'target DNA', the hybridization produces a unique fluorescent signal which may also be detected by the flow cytometer as the bead passes through. Therefore hybridization in hundreds or thousands-of diverse genes can be rapidly detected, quantified and analyzed by this procedure.

Microbeads for flow cytometry are commercially available by several manufacturers (e.g. Polysciences; Molecular Probes). A typical microbead consists of an approximately spherical polystyrene 'core' with a diameter of 0.1-20 µm. The microbead can be tagged with indicator molecules such as fluorescent probes of appropriate wavelength, which are either directly bound to the microbead surface, or bound to a nucleic acid that coats the microbead surface, or fill the 'interior volume' of the microbead. When the microbead passes through the laser beam in a flow cytometer, an intense fluorescent signal is emitted, which is filtered and counted with a photomultiplier. Depending on constraints set by the user (e.g. certain intensity in the observed signal; or a certain combination of emitted fluorescent wavelengths) microbeads can be sorted into separate containers after passage through the cytometer laser beam.

Microbeads can readily be tagged with specific DNA fragments. A standard method to achieve this is to manufacture microbeads with 'functionalized surfaces', e.g. coated with carboxyl- or amino-groups, or with avidin, etc. Such microbeads are widely available. Binding of a nucleic acid on the functionalized surface is achieved via end-labeling the nucleic acid, which is then attached to the microbead surface. For example, if a primary amine is attached to the nucleic acid, then a carbodiimide-mediated reaction can attach the nucleic acid to the carboxyl-coated microbead. If a biotin is attached to the nucleic acid, then this will bind to the avidin-coated microbead, etc. The single stranded DNA attached to the microbeads will be called hereafter 'control DNA'.

When microbeads coated with control DNA are mixed and allowed to hybridize with single stranded 'target DNA' which is to be analyzed for gene expression, polymorphisms or mutations, hybridization will take place if a sequence complementary to the control DNA sequence exists. Hybridization should preferably be under conditions of at least moderate stringency, more preferably high stringency. These conditions can be obtained by varying salts, temperature, etc. and are well known in the art. See e.g., *Sambrook*, et al, *Molecular Cloning Second Edition*. The unhybridized DNA can then be removed from the solution, e.g. via centrifugation, if desired. (This is not an absolute requirement since flow cytometry will only count fluorescence bound to the microbeads and not in solution). Such hybridization of DNA in microbead-format is well known to those experienced in the art, (e.g. to isolate mRNA, poly-dT-coated microbeads are used). To detect signals from microbeads containing hybridized double stranded sequences the target DNA can be pre-labeled with a fluorescent probe. Accordingly, fluorescent signals from microbeads with control DNA hybridized to target DNA can be readily detected via flow cytometry.

In one embodiment, beads can also be labeled with a 'cocktail' of fluorescent probes, each fluorescent probe having a specific emission intensity (Such probes are often used for calibration purposes). Multiparametric flow cytometry, which is a common application, can simultaneously acquire signals from all fluorescent probes bound to the beads and measure their intensity.

For example, a flow cytometer can monitor simultaneously 6 fluorescent emission wavelengths (e.g. by using 3 excitation lasers with two different filters each). The bead can be labeled with, for example, fluorescent probes 1-5 chosen so that they have either distinct excitation or distinct emission wavelengths, with minimal overlap regions. Different amounts of each fluorescent probe can be incorporated on the bead, so that at least 20 distinct fluorescent intensities can result per probe.

Accordingly, in this example there are up to 3,200,000 combinations of beads that can be constructed, each one different from the others, which upon passage through a flow cytometer would give a unique optical signature. (In practice one will not need to use so many combinations, as there are only about 70,000 human genes most of which may not need to be counted in a particular application. A typical application may utilize 1,000 human genes, represented by 1,000-20,000 different beads, each bead containing a different section of a gene).

If each bead is tagged with a different gene, or gene fragment, any desired number of genes can be analyzed in a single experiment, via flow cytometry. Assume also, that the 'target DNA' which is hybridized to the beads of known optical signature tagged with 'control DNA' is tagged with a 6th fluorescent probe, which gives a unique signal, clearly distinguishable from signals by probes 1-5. Upon passage through a multiparametric flow cytometer, each bead would yield (a) its optical signature by monitoring the intensity of emissions from probes 1-5, and thereby the identity of the control gene bound to the bead; and (b) the intensity of emission from probe 6 which would determine if, and to what extent the target DNA has hybridized to the control gene.

The flow cytometer used preferably has the ability to detect 'rare events'. Each B.U.S. will only rarely emit its unique optical signal since other beads will be counted most of the time. If 10,000 distinct B.U.S. are included in an aliquot, representing 1,000 human genes, the flow cytometer must be able to detect and discriminate 1 in $10^4$ beads, without 'noise'. This is well within the capabilities of common flow cytometers, which can typically discriminate 1 in $10^5$ events.

In some embodiments, enhanced software and computer storage space may be needed to record each event separately and store it in an appropriate 'bar histogram' (each bar representing a unique gene). Such software currently exists for applications that deal with a limited number of uniquely labeled beads/cells. The current invention requires that the software handles thousands of different parameters, following the optical detection of unique signatures from a total of $10^7$ to $10^8$ beads. Extension of the current software and disk storage space to satisfy the demands of the current application can readily be accomplished.

Several control genes and beads can be included in the flowcytometric determination, in order to ensure that the method performs optimally.

The above method can be adapted for the detection of SNPs, mutations and methylation. In this approach, an intermediate step is used to isolate and purify only those DNA fragments that contain SNPs, mutations or methylation. This process can be carried out with the compounds and methodologies detailed herein.

Following isolation of those cDNA fragments (typically 50-200 base pair long fragments) that contain alterations, the target DNA is hybridized to control DNA-containing B.U.S.-aliquots and processed via flow cytometry. The optical signature of those beads that present positive signals from probe 6 define the genes that contain SNPs and mutations in the population.

In order to detect SNPs and mutations, the control DNA which is attached to the beads has to be relatively short (e.g. in the region 10-100 base pairs) so that, following capture of a corresponding fragment that contains an SNP/mutation, the genomic region containing the genetic alteration is automatically defined with a good resolution (~100 base pairs). In addition, for each gene that will be examined, enough regions of the gene have to be immobilized (each region on a separate B.U.S.), so that the whole gene (from 3' to 5'-end) is adequately represented at regular intervals. In this manner, every target DNA fragment which is isolated and contains a genetic alteration will be assured of finding a complementary sequence to hybridize in the B.U.S.-aliquot.

B.U.S. can be constructed with optimized properties and sold in a kit, for example, en masse manufacture by a commercial supplier. The kit can have reagents to attach multiple fluorophores and specific DNA sequences on a bead coated with streptavidin for use with biotin-end-labeled oligonucleotides for attachment to streptavidin—binding sites, as well as cocktails of amine-reactive fluorescent probes (e.g. succinimidyl esters of fluorescent probes) for the simultaneous attachment to the free primary amines of streptavidin. Alternatively, on carboxylic acid-coated beads, both the fluorescent compounds and amine-end-labeled nucleic acids can be attached.

The user can decide which and how many genes and which controls are included in each individual experiment, and can change the genes included 'at a moment's notice', in the next experiment. This is currently impossible with chip microarray technology. Furthermore the technique should be significantly cheaper than current chip microarray technology, as the manufacturing or reading of the beads does not entail sophisticated procedures, while the demand is anticipated to be very high.

In still another embodiment, multiple subsets of non-fluorescent microbeads are engineered, each subset tagged with numerous copies of a distinct single stranded DNA ('Control DNA, e.g. a gene; or a specific gene fragment; or an oligonucleotide representing a gene fragment). Numerous single strands of control DNA from each specific gene can be attached to the functionalized surface of a microbead as described above. Alternatively, oligonucleotides of a specific sequence can be attached on the microbead, or grown directly on the microbead using phosphoramidite chemistry which is established in the field of DNA synthesis. The size of this 'control cDNA' on the microbead surface can be of any length, but preferably such that it ensures maximum hybridization with a corresponding 'target cDNA' that has a complementary sequence. Large amounts of the same microbead carrying a single DNA sequence can then be manufactured. Next, a second microbead is selected and the process repeated for a second gene/fragment of interest. By repeating the procedure several times (e.g. 1,000 times), stocks of microbeads each carrying a unique DNA sequence are manufactured. The process can readily be automated.

As explained above, the gene immobilized on the microbead hybridizes to a labeled DNA, e.g., a 'fluorescently labeled target DNA', the hybridization produces a unique fluorescent signal which may be detected by the flow cytometer as the microbead passes through, and then the microbead is appropriately sorted. Therefore several millions microbeads emitting fluorescent signals, representing hundreds or thousands of diverse genes in the target DNA, can be rapidly detected and separated from non-fluorescent microbeads by this procedure.

A collection of individuals with a specific pathology can be screened for a common genetic trait (e.g. common set of unknown mutations/polymorphisms in an unknown set of genes) because the present invention allows the isolation and identification of only those genes that appear in common in the patient population. For example, for a set of 5 patients having early-age lung cancer, and for whom an inherited set of unknown mutated genes can be hypothesized.

DNA from a tissue sample (e.g. lymphoblasts) from each patient is extracted. The DNA is then enzymatically digested into small fragments (e.g. 50-200 base pairs). Third, those fragments that contain polymorphisms (mutations) that appear as heterozygosities among the two alleles, are selected and isolated from the population of non-mutated DNA fragments. One preferred procedure to accomplish this task is the one described above using aldehyde-linker based methods, and will not be further addressed here. Another less preferred possibility is to utilize any other described technology that can 'capture' and isolate the heterozygous sequences, while discarding the non-mutant sequences. A combination of the above technologies is also possible. The 'target' DNA selected from each affected individual for polymorphism screening may be only from one gene; or preferably from several genes or from the whole cDNA library, or from the whole genome.

Following isolation of mutant fragments from each individual, the fragments are PCR-amplified using primers which are labeled with a fluorescent probe, or combination of probes. Thus, each of the 5 individual's mutant DNA is labeled with a different fluorescent probe from that of another member of the group, or combination of their probes, appropriate for flow cytometry (7-hydroxycoumarin; fluorescein; rhodamine; Texas Red; Bodipy; etc).

The fluorescently-labeled DNA from the 5 individuals is then mixed together and hybridized with microbeads engineered as described above. As described above, each subset of microbeads carries a specific gene (or gene fragment) as a 'control' DNA. Let us assume for simplicity that only one subset of microbeads is included, representing only one gene fragment. Each such microbead will allow target DNA from all 5 individuals to bind to it, if the corresponding gene fragment is mutated in all 5 individuals simultaneously. This microbead will emit all 5 fluorescent wavelengths when screened via flow cytometry, and therefore can be sorted and separated from microbeads with 4, 3, 2, 1 or none fluorescent emissions.

If instead of one, several subsets of microbeads representing numerous genes are utilized, the procedure remains unchanged. The flow cytometer will sort in the same container all microbeads (i.e. all genes, irrespective of their identity) that present fluorescent signals from a set percentage, e.g., all 5 fluorescent probes (i.e. genes from all 5 individuals). These are the genes of interest, i.e. the mutated genes that are likely to be the cause of the common disease in the patient population.

To discover the identity of these common genes, following flow cytometry the sorted microbeads are used in a PCR reaction to amplify the DNA fragments immobilized on them. By the design of the procedure followed for isolation of the mutant fragments, each fragment is flanked by the same, known PCR primers (see DFCI patent previously submitted). Finally, following PCR, the amplified fragments can be identified by a single application on a DNA microarray such as those that are currently commercially available, or preferably those described above.

Thus, the present procedure allows the isolation and identification of those mutated/polymorphic genes that appear in common in the affected patient population, and therefore have an increased probability to be related (or to be the cause) of the specific disease. Although the mutated/polymorphic genes in any single individual are likely to be many (e.g. 100,000 polymorphisms across the whole cDNA), the common genes are likely to be much fewer in number, since they must appear in common in all 5 individuals. The more individuals are simultaneously screened with the present method, the fewer the 'common' mutated genes are going to be, therefore the faster the 'disease genes' will be identified.

If more than 5 individuals are to be screened for common mutated genes with the present method, the flow-cytometric method again can be applied as follows: First, DNA from 5 individuals is fluorescently labeled and screened as described above. The sorted microbeads corresponding to genes mutated in all 5 individuals is then briefly treated to remove the fluorescence (e.g. via heating for 2 min, 96° C., to remove the fluorescent strand; or via an enzyme that removes the DNA segment containing the fluorescent probe; etc). These microspheres are then again processed via the same procedure, to screen 5 more individuals: they are mixed with the labeled DNA from these individuals, to hybridize to mutated genes; then they are sorted via flow cytometry to select those microbeads that emit all 5 fluorescent signals. These represent microbeads that have captured mutant genes both in the first and in the second set of 5 individuals, and they now represent genes that are mutated in all 10 (5+5) individuals. By repeating the procedure more individuals can be screened. Ultimately the number of sorted microbeads will decrease significantly, and should correspond to the few 'disease-specific genes' that are sought.

It is possible however that, although a mutated gene may be involved in the causes of cancer in most individuals, it is not required for cancer formation. Therefore it may only appear as a mutated gene in 80% of cancers. A significant feature of the present invention is that, apart from identifying genes that are mutated in all individuals, it also allows for mutated genes that appear in most but not all individuals to be identified. For example, flow-cytometric sorting of the microspheres can be adjusted so that if 2 out of signals, more preferably, 3 out of 5 signals are present in a single microsphere this is also selected in a separate container. One can readily select a particular cut-off percent. Similarly, if the mutated gene is present in 4 out of 5 individuals it will also be sorted, etc. In this manner, not only genes mutated in 100% of the patients, but also genes mutated in preferably 50%, or more preferably 60%, etc, will also be identified. Still more preferably the mutation is present in 80% of the members. Higher percentages will be seen when the group is composed of related individuals.

A practical advantage of utilizing flow cytometry and microbeads for the present approach is that, because the DNA is not immobilized on 'inflexible' DNA chips but on individual microbeads, the user has full control over which genes and controls will be included in his study, thereby the method can be adjusted to the needs of a particular application, on an experiment-by-experiment basis.

In an alternative application, instead of searching for common mututatios/polymorphisms in a patient population, common expression of specific sets of genes is sought (e.g. common genes up- or down-regulated in cancer tissues, or in a set of patients with susceptibility to lung cancer, etc).

To utilize the present invention for this purpose, a similar flow-cytometric analysis can be applied. Briefly, the cDNA generated from each individual is enzymatically fragmented, denatured and ligated with PCR primers tagged with a unique fluorescent probe, or combination of probes. The labeled, single stranded cDNA molecules from several individuals are then mixed together and incubated with microbeads designed and described above. The described flow-cytometric process is then applied to sort microspheres that present signals from all individuals simultaneously, signifying combined up-regulation of a specific gene in all individuals. Certain signal intensities can be selected as a 'threshold' above which a gene is considered as up-regulated (i.e. many copies bound to microbead) or down-regulated. Both commonly up-regulated and down-regulated genes in the population are bunched together and sorted in separate containers in this procedure. Therefore by following the protocol described above for deriving common mutations in the population, the genes that are up-regulated or down-regulated in common can also be identified.

Although flow cytometry is a preferred and very convenient embodiment of this invention, it has limitations as to how many fluorescent signals can be simultaneously detected each time a microsphere is measured, and how many different fluorophores can be used. With typical flow cytometers, 5-7 signals can be simultaneously measured; therefore each flow-cytometric measurement can readily detect common genes in 5-7 individuals, and the procedure can be repeated to screen additional individuals. For screening a population of 50 patients, the procedure typically needs to be repeated 7-10 times. Specialized flow-cytometers that can screen more than 5-7 signals simultaneously also exist, and these can increase the efficiency of this procedure.

Alternatively, the combined signals from microspheres can be detected with a different detection system, such as an ICCD camera, a microscope, or a photomultiplier that detects several wavelengths simultaneously.

Several control genes and microbeads can preferably be included in the flow-cytometric determination, in order to ensure each time that the method performs optimally.

Kits

A preferred kit will comprise all reagents required to perform the method of the present invention. For example, the kit can contain the reagents needed to isolate mRNA from tissues, synthesize cDNA, carry out the steps described to remove the 5'P groups, etc., perform PCR to detect mismatches, isolate mutant/polymorphic fragments, and finally apply on an array to detect the alterations at specific genomic positions.

The kit can be used to screen an individual for inherited susceptibility to cancer, cardiovascular disease, neurodegenerative disorders, etc. by mapping positions of heterozygosities and SNPs in the whole genome or in selected fractions of the genes.

In a preferred embodiment, PCR primers would also be included.

In one embodiment, kits for carrying out the identification of these DNA mismatches with these beads can be sold. The kits would include the enzymes or chemicals to cleave the nucleic acid at sites of mismatch, reagents to perform PCR and preferably instructions. These materials can be in any vial. The materials can be in lyophilized form.

EXAMPLE 1

Enablement of Single Gene Mutation Detection

Figure 5:
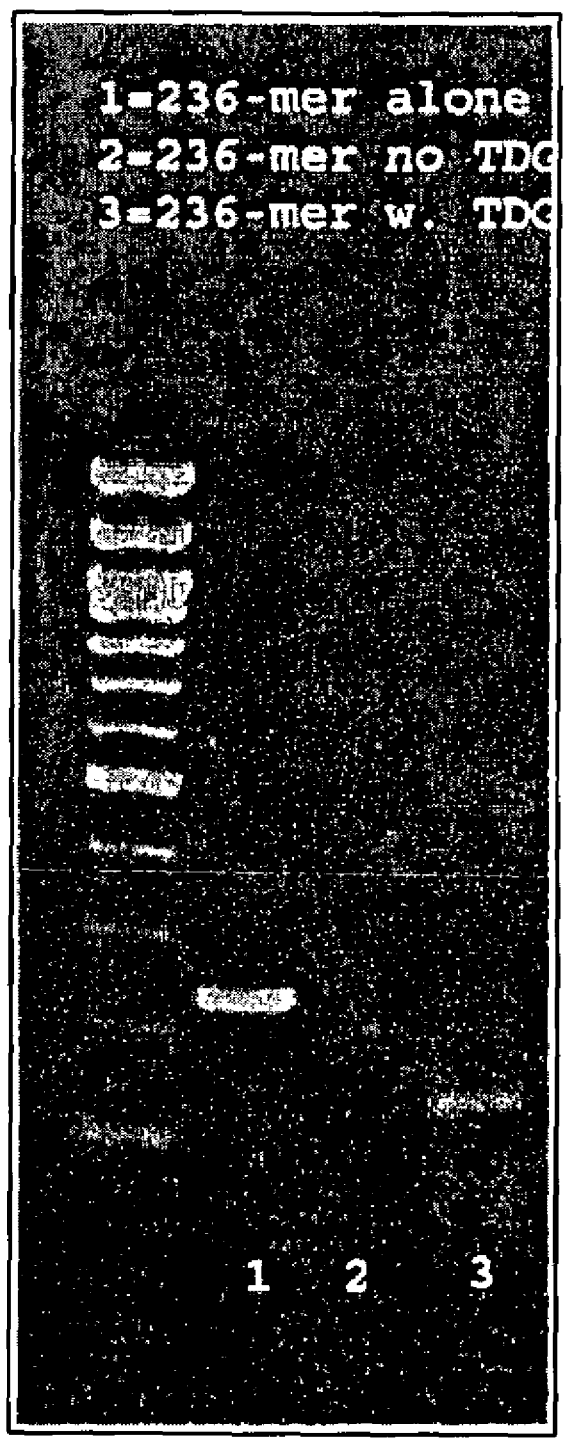
FIG. 5 shows a gel demonstrating detection of a single G-to-A mutation in the p53 gene using the method of the present invention.

FIG. 5 demonstrates application of the method of the present invention for detection of a G-to-A mutation in the p53 gene. A 236 bp PCR fragment (lane 1) was PCR amplified from a p53 gene known to be heterozygous for this mutation. The *Ecoli* TDG (Trevigen) is an enzyme known to remove thymidine from G:T mismatches. G:T mismatches form whenever a G:C and an A:T-containing fragment are cross-hybridized, i.e. are expected to form in the present heterozygous situation. By application of the described protocol, an extra band was generated when the enzyme TDG was used (lane 3). No band is detected when no TDG is used (lane 2). The extra band demonstrates successful detection of the mutation.

EXAMPLE 2

Enablement of Single Gene Mutation Detection

Figure 9:
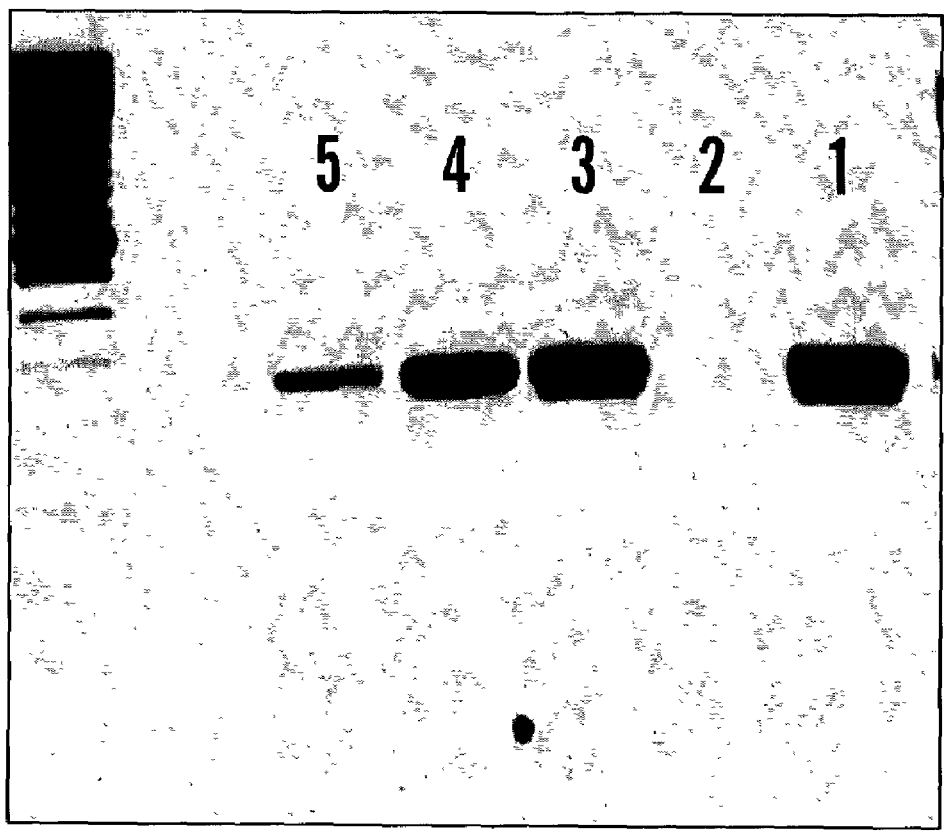
FIG. 9 shows detection of G to A mutations in the Ku gene. Genomic DNA from 2 individuals, one heterozygous (mutant) and one homozygous (normal) for a specific Ku gene position, was PCR amplified using a high fidelity polymerase. The presence of the mutation generates a new recognition site (GATC) for the restriction enzyme SAU, which allows application of the PCR-RFLP-RCR approach. As in FIG. 6, a primer was ligated at the mutation position following SAU-digestion of the amplified PCR product. Ligation of the primer allowed subsequent PCR amplification of only the heterozygous sample. The mutant and normal DNAs were mixed at ratios ranging from 1:4 mutant: normal DNA (in lane 1) to 1:20,000 (in lane 5).
Figure 10:
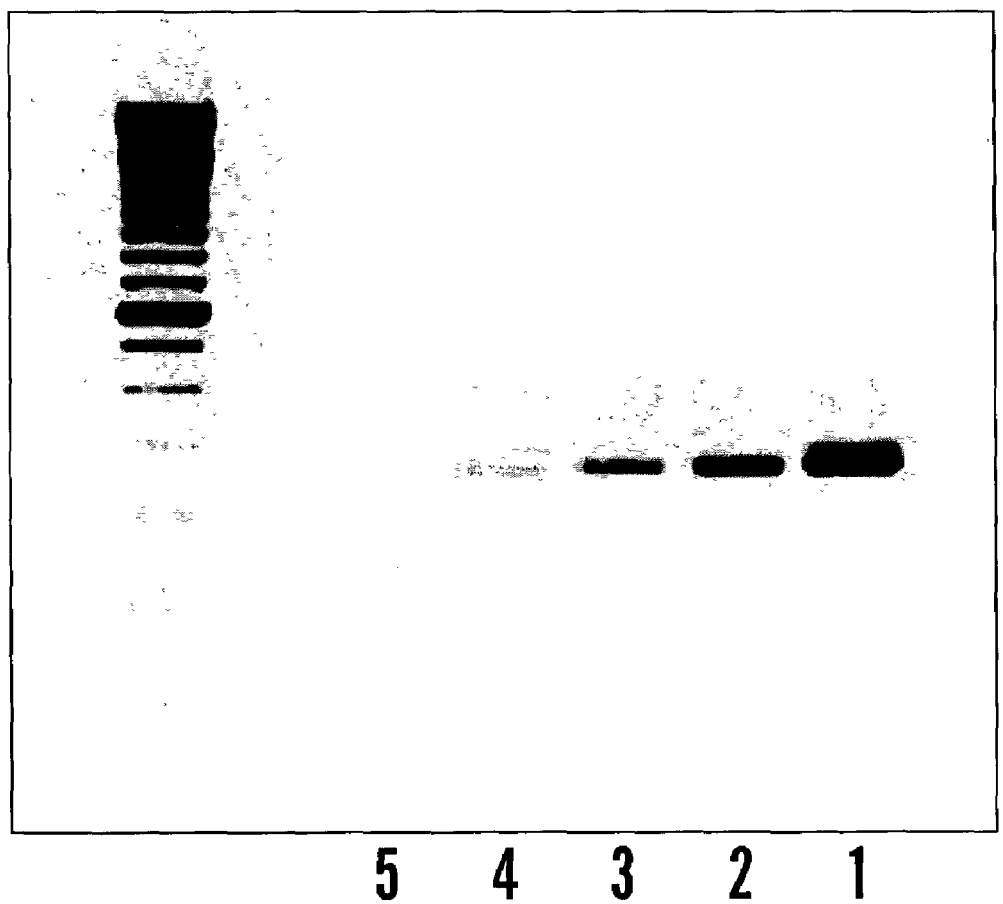
FIG. 10 shows detection of G to A mutations in the Ku gene. Genomic DNA from 2 individuals, one heterozygous (mutant) and one homozygous (normal) for a specific Ku gene position, was PCR amplified using a high fidelity polymerase. The presence of the mutation generates a new recognition site (GATC) for the restriction enzyme SAU, which allows application of the PCR-RFLP-RCR approach. As in FIG. 6, a primer was ligated at the mutation position following SAU-digestion of the amplified PCR product. Ligation of the primer allowed subsequent PCR amplification of only the heterozygous sample. The mutant and normal DNAs were mixed at ratios ranging from 1:4 mutant: normal DNA (in lane 1) to 0.6:1,000,000 (in lane 4).

FIGS. 9 and 10 demonstrate application of the method of the present invention for detection of a G-to-A mutation in the Ku gene. Mutations could be detected where there were 1,000,000 copies of the normal, wild type allele for every 0.6 copy of the mutant allele.

Figure 6:
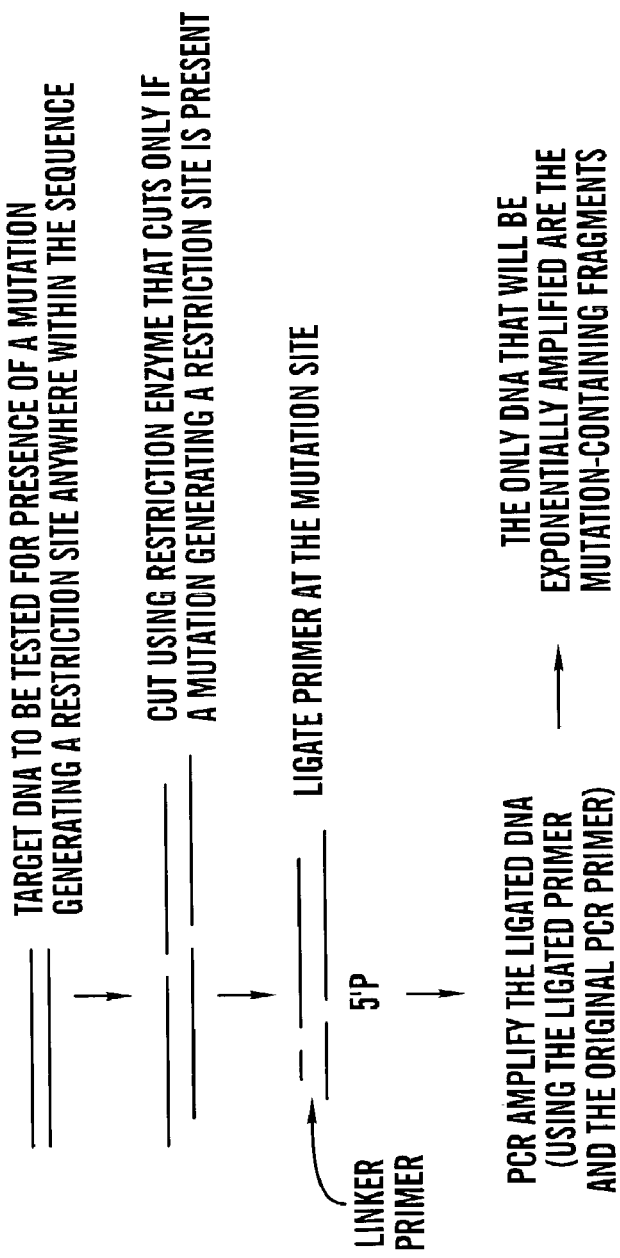
FIG. 6 shows a schematic of a variation in the present technology to screen for mutations in a single gene, in which a restriction enzyme is used to detect mutations which generate a recognition sequence for the restriction enzyme which is not present in the wild-type allele.

In FIG. 9, genomic DNA from 2 individuals, one heterozygous (mutant) and one homozygous (normal) for a specific Ku gene position, was PCR amplified using a high fidelity polymerase. The presence of the mutation generates a new recognition site (GATC) for the restriction enzyme SAU, which allows application of the PCR-RFLP-RCR approach. As in FIG. 6, a primer was ligated at the mutation position following SAU-digestion of the amplified PCR product. Ligation of the primer allowed subsequent PCR amplification of only the heterozygous sample. The mutant and normal DNAs were mixed at ratios ranging from 1:4 mutant: normal DNA (in lane 1) to 1:20,000 (in lane 5).

In FIG. 10, genomic DNA from 2 individuals, one heterozygous (mutant) and one homozygous (normal) for a specific Ku gene position, was PCR amplified using a high fidelity polymerase. The presence of the mutation generates a new recognition site (GATC) for the restriction enzyme SAU, which allows application of the PCR-RFLP-RCR approach. As in FIG. 6, a primer was ligated at the mutation position following SAU-digestion of the amplified PCR product. Ligation of the primer allowed subsequent PCR amplification of only the heterozygous sample. The mutant and normal DNAs were mixed at ratios ranging from 1:4 mutant: normal DNA (in lane 1) to 0.6:1,000,000 (in lane 4).

All references discussed herein are incorporated herein by reference.

REFERENCES

1. Gerry, N. P., N. E. Witowski, J. Day, R. P. Hammer, G. Barany, and F. Barany, *Universal DNA microarray method for multiplex detection of low abundance point mutations.* J Mol Biol, 1999. 292(2): p. 251-62.
2. Khanna, M., W. Cao, M. Zirvi, P. Paty, and F. Barany, *Ligase detection reaction for identification of low abundance mutations.* Clin Biochem, 1999. 32(4): p. 287-90.
3. Pfeifer, G. P., M. F. Denissenko, and M.S. Tang, *PCR-based approaches to adduct analysis.* Toxicol Lett, 1998. 102-103: p. 447-51.
4. Lizardi, P. M., X. Huang, Z. Zhu, P. Bray-Ward, D. C. Thomas, and D. C. Ward, *Mutation detection and single-molecule counting using isothermal rolling-circle amplification.* Nat Genet, 1998. 19(3): p. 225-32.

I claim:

1. A method of identifying at least two nucleic acid alterations in a single target nucleic acid, which comprises:
   (a) preparing the target nucleic acid and a control nucleic acid;
   (b) hybridizing the target nucleic acid with the control nucleic acid to create a heteroduplex, wherein the control nucleic acid is the wild type nucleic acid corresponding to the target nucleic acid, and wherein a mismatch is formed between the control and the target nucleic acid at each location where a difference is present;
   (c) removing any 5' phosphate groups or 3' hydroxyl groups from the heteroduplex nucleic acid ends by circularizing said heteroduplex nucleic acid and selectively degrading any non-circularized heteroduplex nucleic acids;
   (d) cleaving said circularized heteroduplex nucleic acid at the site of any mismatch using any agent that generates a single or double strand break at the site of the mismatch, thereby creating free 5'P or 3'OH ends at the site of said any mismatch;
   (e) ligating a linker at the 5' phosphate group at any of the newly generated 5' phosphate groups, or ligating a linker at any of the newly generated 3' hydroxyl groups;
   (f) selectively amplifying the cleaved, heteroduplex nucleic acid fragments which have a linker ligated thereto using a polymerase chain reaction; and
   (g) determining if at least two different nucleic acid fragments are present to identify the at least two nucleic acid alterations present in the target nucleic acid.

2. The method of claim 1, wherein the nucleic acid is selected from the group consisting of cDNA, genomic DNA, PCR-amplificatian product, and mRNA.

3. The method of claim 1, wherein the PCR-amplification product is further amplified using a high fidelity polymerase and the primers used to generate the product are not phosphozylated at the 5' end.

4. The method of claim 1, wherein the agent in step (d) is any restriction enzyme that does not generate blunt ends.

5. The method of claim 1, wherein the preparation of the target and control nucleic acid further comprises ligating a double stranded linker onto each nucleic acid, wherein said double stranded linkers are synthetic complementary linkers which do not contain 5' phosphate groups.

6. The method of claim 5, wherein the preparation of the target and control nucleic acid further comprises PCR amplification of the nucleic acid.

7. The method of claim 1, wherein the target and control nucleic acids are hybridized in the presence of hydroxylamine.

8. The method of claim 1, wherein the agent that generates strand breaks at sites of mismatch is selected from the group consisting of chemical agents, enzymes, and a combination of a chemical agent and an enzyme.

9. The method of claim 8, wherein the chemical agent is selected from the group consisting of hydroxylamine, osmium tetroxide, potassium permanganate, tetraethyl ammonium acetate, hydrazine, and carbodiimide, and wherein the site of cleavage is further treated with piperidine to generate a 5' P at the strand break.

10. The method of claim 8, wherein the enzyme is selected from the group consisting of glycosylase, resolvases, cleavases, ribonucleases, and nucleases.

11. The method of claim 8, wherein the enzyme selected is a restriction endonuclease that identifies a restriction site not present in the control nucleic acid.

12. The method of claim 11, wherein the restriction site is an additional restriction site of a restriction site present in the control nucleic acid.

13. A method of identifying at least two nucleic acid alterations in a single target nucleic acid, which comprises:
   (a) preparing a target nucleic acid that comprises a specific recognition sequence for a restriction endonuclease enzyme, wherein its wild-type allele lacks;
   (b) hybridizing the target nucleic acid with a control nucleic acid to create a heteroduplex, wherein the control nucleic acid is the wild type allele corresponding to the target nucleic acid and wherein a mismatch is formed between the wild type and the target nucleic acid whenever a difference is present;
   (c) removing any 5' phosphate groups or 3' hydroxyl groups from the heteroduplex nucleic acid ends by circularizing said heteroduplex nucleic acid and selectively degrading any non-circularized heteroduplex nucleic acids;
   (d) cleaving said circularized heteroduplex nucleic acid with a restriction endonuclease enzyme to create a double strand break at the site of any mismatch, generating free 5'P or 3'OH ends at the site of said any mismatch;
   (e) ligating a linker at any of the newly generated 5' phosphate groups at the sites of cleavage when 5' phosphate groups have been removed, or ligating a linker at any of the newly generated 3' hydroxyl groups at the site of cleavage, when 3' hydroxyl groups have been removed;
   (f) selectively amplifying the nucleic acid fragments amplified in step (e) to identify if at least two alterations are present, wherein the selective amplification of the nucleic acid fragments is performed via nested-PCR using primers internal to the nucleic acid fragments.

14. The method of claim 13, wherein the restriction endonuclease is a four-base cutter enzyme.

15. The method of claim 14, wherein the restriction endonuclease is selected from the group consisting of N1AIII, SAU3A1, TaqI, MaeII, MaeI and MseI.

16. The method of claim 13, wherein the target nucleic acid is selected from the group consisting of cDNA, genomic DNA, PCR-amplification product and mRNA.

17. A method of identifying at least two nucleic acid alterations in a single target nucleic acid, which comprises:
   (a) preparing the target nucleic acid and a control nucleic acid;
   (b) hybridizing the target nucleic acid with the control nucleic acid to create a heteroduplex, wherein the control nucleic acid is the wild type nucleic acid corresponding to the target nucleic acid and wherein a mismatch is formed between the wild type and the target nucleic acid whenever a difference is present;
   (c) removing any 5' phosphate groups or 3' hydroxyl groups from the heteroduplex nucleic acid ends;
   (d) cleaving the heteroduplex nucleic acid at the site of any mismatch using any combination of agents that generate blunt-ended double strand breaks at the site of mismatch thereby creating free 5'P or 3'OH ends at the site of any mismatch;
   (e) ligating a linker at any of the 5' phosphate group at the newly generated 5' phosphate groups at the site of cleavage when 5' phosphate groups have been removed, or ligating a linker at any of the newly generated 3' hydroxyl groups at the site of cleavage when 3' hydroxyl groups have been removed;

(f) selectively amplifying the nucleic acid fragments which have a linker ligated thereto using polymerase chain reaction; and (g) detecting if at least two different nucleic acid fragments are present to identify the at least two alterations in the target nucleic acid, wherein following cleavage of the heteroduplex nucleic acid at the site of mismatch, S1 nuclease is used to convert any single strand breaks to blunt-ended double strand breaks.

* * * * *